(12) United States Patent
Fitzpatrick et al.

(10) Patent No.: US 11,752,088 B2
(45) Date of Patent: *Sep. 12, 2023

(54) HIGHLY CONCENTRATED SEAWATER MINERAL EXTRACT AND USES THEREOF

(71) Applicant: Oriel Seasalt Company Limited, Drogheda (IE)

(72) Inventors: Brian Fitzpatrick, Dublin (IE); John Delany, Laytown (IE)

(73) Assignee: Oriel Seasalt Company Limited, Drogheda (IE)

( * ) Notice: Subject to any disclaimer, the term of this patent is extended or adjusted under 35 U.S.C. 154(b) by 606 days.

This patent is subject to a terminal disclaimer.

(21) Appl. No.: 15/739,546

(22) PCT Filed: Jun. 24, 2016

(86) PCT No.: PCT/EP2016/064763
§ 371 (c)(1),
(2) Date: Dec. 22, 2017

(87) PCT Pub. No.: WO2016/207411
PCT Pub. Date: Dec. 29, 2016

(65) Prior Publication Data
US 2018/0177714 A1    Jun. 28, 2018

(30) Foreign Application Priority Data

Jun. 24, 2015  (IE) .................................. S2015/0187

(51) Int. Cl.
*C02F 9/00*     (2023.01)
*C02F 1/00*     (2023.01)
(Continued)

(52) U.S. Cl.
CPC .............. *A61K 8/965* (2013.01); *A61K 8/042* (2013.01); *A61K 9/06* (2013.01); *A61K 33/06* (2013.01);
(Continued)

(58) Field of Classification Search
None
See application file for complete search history.

(56) References Cited

U.S. PATENT DOCUMENTS 5,955,067 A  *  9/1999  Oge  ..................... A61Q 19/008
                                                424/78.07
7,652,000 B2 *  1/2010  Perry ..................... A61K 31/69
                                                514/64
(Continued)

FOREIGN PATENT DOCUMENTS

CA    2650368 A1 *  7/2010  ............. A61K 33/00
CA    2650368 A1    7/2010
(Continued)

OTHER PUBLICATIONS

Machine translation of CN-106265144-A, 2010. (Year: 2010).*
(Continued)

*Primary Examiner* — Carlos A Azpuru
*Assistant Examiner* — Casey S Hagopian
(74) *Attorney, Agent, or Firm* — LaBatt, LLC

(57) ABSTRACT

A seawater mineral extract derived from seawater having a salinity of from 3.4% Brix to 3.6% Brix, wherein the seawater mineral extract comprises a mineral salt content of at least 20% of the overall seawater extract.

11 Claims, 10 Drawing Sheets

Control          0.4% Oriel Mg Mineral Complex

(51) Int. Cl.

| | |
|---|---|
| *C02F 1/38* | (2023.01) |
| *C02F 1/04* | (2023.01) |
| *C02F 1/26* | (2023.01) |
| *C02F 1/44* | (2023.01) |
| *C02F 103/08* | (2006.01) |
| *A61K 8/96* | (2006.01) |
| *A61Q 7/00* | (2006.01) |
| *A61Q 19/00* | (2006.01) |
| *A61Q 19/08* | (2006.01) |
| *A61K 9/06* | (2006.01) |
| *A61K 8/04* | (2006.01) |
| *A61K 45/06* | (2006.01) |
| *A61K 33/30* | (2006.01) |
| *A61K 33/06* | (2006.01) |
| *A61K 47/10* | (2017.01) |
| *A61K 33/26* | (2006.01) |
| *A61K 33/34* | (2006.01) |
| *A61K 35/08* | (2015.01) |

(52) U.S. Cl.
CPC ............. *A61K 33/26* (2013.01); *A61K 33/30* (2013.01); *A61K 33/34* (2013.01); *A61K 35/08* (2013.01); *A61K 45/06* (2013.01); *A61K 47/10* (2013.01); *A61Q 7/00* (2013.01); *A61Q 19/00* (2013.01); *A61Q 19/004* (2013.01); *A61Q 19/08* (2013.01); *C02F 1/001* (2013.01); *C02F 1/38* (2013.01); *C02F 9/00* (2013.01); *C02F 1/04* (2013.01); *C02F 1/265* (2013.01); *C02F 1/385* (2013.01); *C02F 1/441* (2013.01); *C02F 2103/08* (2013.01)

(56) References Cited

U.S. PATENT DOCUMENTS

| | | | | |
|---|---|---|---|---|
| 10,843,951 | B2* | 11/2020 | Fitzpatrick | ................ C25B 1/34 |
| 2006/0099239 | A1* | 5/2006 | Coleman | .............. A61K 31/353 424/440 |
| 2006/0251605 | A1* | 11/2006 | Belmar | .................. A61K 8/342 424/70.22 |
| 2014/0193524 | A1* | 7/2014 | Willeford | ............... A61K 33/00 424/681 |

FOREIGN PATENT DOCUMENTS

| | | | |
|---|---|---|---|
| CN | 106265144 | A * | 1/2017 |
| JP | 2001072526 | A | 3/2001 |
| WO | 2015/092025 | A1 | 6/2015 |

OTHER PUBLICATIONS

Holzman, B.A. Aquatic Biomes, Geography 316.01 slides, San Francisco State University, 2005, pp. 1-7, accessed online on Sep. 8, 2020 at <http://online.sfsu.edu/bholzman/_private/316_05/5-Aquatic%20biomes.pdf>. (Year: 2005).*

Esslemont, G. "Heavy metals in seawater, marine sediments and corals from the Townsville section, Great Barrier Reef Marine Park, Queensland", Marine Chemistry, 71, 2000, pp. 215-231. (Year: 2000).*

Safety Data Sheet for Artificial Seawater accessed online on Sep. 8, 2020 at www.lakeproductscompany.com. (Year: 2019).*

"Magnesium Chloride", Solubility of Things, accessed online on Jul. 31, 2021 at https://www.solubilityofthings.com/water/ions_solubility. (Year: 2021).*

"Ancient Minerals Ultra Magnesium Oil 237ml", GPA Wholefoods, accessed online on Jul. 31, 2021 at https://www.gpawholefoods.com.au/buy/ancient-minerals-ultra-magnesium-oil-237ml/AM-MAG-OIL. (Year: 2021).*

"Solubility of salts (ions)", Solubility of Things, accessed online on Jul. 31, 2021 at https://www.solubilityofthings.com/water/ions_solubility. (Year: 2021).*

Madden, C. "What makes Oriel Sea Salt different from the rest", The Irish Times, Dec. 10, 2014, accessed online at https://www.irishtimes.com/business/agribusiness-and-food/what-makes-oriel-sea-salt-different-from-the-rest-1.2031570. (Year: 2014).*

McKenna, S. "Salt of the earth", The Irish Times, Oct. 19, 2013, accessed online at https://www.irishtimes.com/salt-of-the-earth-1.1561409. (Year: 2013).*

"Condiments" La Rousse Foods, 2015, accessed online https://www.laroussefoods.ie/pdf/Condiments%202015.pdf. (Year: 2015).*

"Earning their salt: Seriously good product sets Oriel apart", Independent.ie, Feb. 2015, accessed at https://www.independent.ie/business/small-business/earning-their-salt-seriously-good-product-sets-oriel-apart-31027156.html. (Year: 2015).*

"About Us", Oriel, 2022, accessed at https://orielnutracueticals.com/about-us.html-:~:text=Oriel%20was%20established%20in%202012,to%20those%20we%20first%20imagined. (Year: 2022).*

Fortune, A. "Linden Foods launches salt moss aged beef range in Marks & Spencer", Food Manufacture, May 2015, accessed online at https://www.foodmanufacture.co.uk/Article/2015/05/21/Linden-Foods-launches-salt-moss-aged-beef-range-in-Marks-Spencer. (Year: 2015).*

Sindel, U., International Application No. PCT/EP2016/064763, International Search Report and Written Opinion, dated Sep. 16, 2016, 10 pages.

Ehrhardt, P., et al., "Bathing in a magnesium-rich Dead Sea salt solution improves skin barrier function, enhances skin hydration, and reduces inflamation in atopic dry skin," International Journal of Dermatology, Feb. 2005, 2 pages, Abstract Only.

Hataguchi, et al., "Drinking deep-sea water restores mineral imbalance in atopic eczema/dermatitis syndrome," European Journal of Clinical Nutrition, Sep. 2005, 11 pages.

Kimata, H., et al., "Improvement of skin symptoms and mineral imbalance by drinking deep sea water in patients with atopic eczema/dermatitis syndrome (AEDS)," 2002, 1 page, Abstract Only.

* cited by examiner

Keratinocyte (KC) media, no cells
KC media + cells
Cells + KC media + 0.1% Oriel
Cells + KC media + 0.2% Oriel
Cells + KC media + 0.4 % Oriel
Cells + KC media + 0.6% Oriel
Cells + KC media + 0.8% Oriel
Cells + KC media + 1.5% Oriel Keratinocyte (KC) media, no cells
KC media + cells
Cells + KC media + 0.1% Oriel
Cells + KC media + 0.2% Oriel
Cells + KC media + 0.4 % Oriel
Cells + KC media + 0.6% Oriel
Cells + KC media + 0.8% Oriel
Cells + KC media + 1.5% Oriel

HIGHLY CONCENTRATED SEAWATER MINERAL EXTRACT AND USES THEREOF

INTRODUCTION

The present invention relates to the use, in a cosmetic, nutraceutical, pharmaceutical, or veterinary composition or for preparing a pharmaceutical, nutraceutical, veterinary or cosmetic composition, of an effective amount of sea minerals or a seawater extract comprising sea minerals.

Sea Salt and seawater extracts are characterised by their origin, in terms of taste, appearance, texture and beneficial properties. Just as grapes are affected by terroir and weather, Sea Salt and seawater extracts are affected by deep water currents, cleanliness, mineral content and purity of the water in the location from which it is sourced and the processes used to make, preserve and refine these characteristics. Sea Salt and seawater extracts comprise of a collection of differing minerals in varying amounts, such minerals are known to have advantageous properties and uses.

The dietary focus on chemical elements derives from an interest in supporting the biochemical reactions of metabolism with the required elemental components. Appropriate intake levels of certain chemical elements have been demonstrated to be required to maintain optimal health. At least twenty mineral chemical elements are known to be required to support human biochemical processes by serving structural and functional roles as well as electrolytes. Chemical elements in order of abundance in the human body include the seven major dietary elements calcium, phosphorus, potassium, sulphur, sodium, chlorine, and magnesium. Important "trace" or minor dietary elements, necessary for mammalian life, include iron, cobalt, copper, zinc, manganese, molybdenum, iodine, bromine, and selenium.

For example Magnesium, Calcium and Zinc are three of the most important minerals essential for good health. Magnesium is a mineral that's crucial to the body's function. It is one of the building blocks that are required for more than six hundred biochemical and enzymatic reactions in the body. Magnesium helps keep blood pressure normal, bones strong, the heart rhythm steady, the transmission of nerve impulses, body temperature regulation and detoxification and energy production. It plays a crucial role in the repair and regeneration of cell tissue while it is a key mineral for the health and is necessary for the efficient absorption of calcium. Multiple health benefits of magnesium include transmission of nerve impulses, body temperature regulation, detoxification, energy production, and the formation of healthy bones and teeth. Magnesium aids in the absorption of calcium by the body, while zinc actively supports the body's immune system. Studies have indicated that besides keeping osteoporosis at bay, magnesium health benefits in women include relief from symptoms of menopause and premenstrual syndrome (PMS). The other crucial health benefits of magnesium include protein and DNA synthesis; relief from bronchospasm (constricted airways) in the lungs; assisting with the prevention and management of cardiovascular diseases; helping regulate high blood pressure (Hypertension); diabetes, migraines, insomnia and depression; and improvement of parathyroid function. Magnesium boosts the bio-availability of vitamin B6 and cholesterol, improves muscle functioning, and assists in the prevention of osteoporosis, insomnia, constipation, heart attacks, hypertension, migraines and kidney stones and gallstones.

One caveat has become apparent, in that the formulation of Mg determines its efficacy and administration. This observation has been reported in its use for gastro-intestinal and obstetric disease and recently cardiovascular and neurological indications. A case in point being that studies of serum/dietary magnesium intake on cardiovascular disease, carotid intima-media thickness (CIMT), hypertension (HTN) and cholesterol synthesis have been investigated and shown to be associated. Despite differences in patient populations, observational and interventional studies have suggested that low serum/dietary magnesium is associated with higher CIMT and more cardiovascular risk factors. A few clinical and basic science interventional studies have also shown the benefits of magnesium administration in cardiovascular disease prevention and as a neuroprotective agent, suggesting a use in the management of age related dementias. Low magnesium levels have been implicated in inflammation and endothelial dysfunction by modulating the interlinked transcription factors (i) NF-κB associated with inflammation, and (ii) Peroxisome proliferator-activated receptors (PPARs) associated in maintaining homeostatic signalling. Hypomagnesemia results in increased C-reactive protein and cytokine exaggeration, increased NF-κB activation, platelet dysfunction, and pathologic PPAR signalling, which can lead to thrombosis, together with the initiating and progression of vascular dysfunction.

With respect to inflammation, endothelial and cell damage Microparticles (MPs), sub-micron vesicles released by all cell via cell activation or apoptosis, could be considered biomarkers of cell damage and activation as well as novel signaling structures. They have been identified both as bio a diagnostic and prognostic indices of many chronic illnesses. Moreover, they have recently been identified as potent signaling mediators. Quantitative and qualitative analysis of MPs is based on antigenic signature and vesicle content, which in turn is dependent on cellular origin and mechanism of release.

Rheumatoid Arthritis (RA) is characterized by immune and endothelial activation, both potentiated by MP bioactivity. MP numbers are increased in RA patients compared to Health controls and positively correlate with associated traditional CV risk factors, similar to that of Cardiovascular and Respiratory subjects.

In addition, frequency of different MP subsets is different in RA patients and significantly associated to disease features. Moreover, in vitro assays reveal that MPs isolated from RA patients were able to promote endothelial activation and modified endothelial cell functionality. Circulating MPs from RA patients display quantitative and qualitative alterations that are the result of both disease-specific and traditional CV risk factors, thus supporting their role as biomarkers of vascular damage.

Healthy cytosolic levels of Mg have been demonstrated to inhibit the enzyme-Calpain, and key mediator in MP generation. As individuals become Hypomagnesic, calpain activation becomes unregulated causing an increase in MP formation. Therefore supplementation of patients with Mg, either orally or topically, may modify the systemic inflammatory response.

Nearly one trillion platelets circulate in the blood to monitor and preserve the integrity of the vasculature. However, haemostasis is not their only function. Platelets are also potent immune cells capable of a range of effector responses. Studies have shown that platelets can have unexpected roles in rheumatic diseases. In patients with rheumatoid arthritis (RA), IL-1-containing platelet-derived vesicles called microparticles (see above) are abundant in arthritic joint fluid. These microparticles can elicit production of inflammatory mediators from resident synovial fibroblasts, which have an integral role in the development of arthritis. Platelets also serve as a source of prostaglandins that contribute to synovial inflammation. Furthermore, serotonin released by platelets helps drive the persistent vascular permeability that characterizes the microvasculature of the inflamed synovium, an unexpected function for a cell that more typically serves as a guardian of vascular integrity. Beyond RA, platelet activation has been observed in systemic lupus erythematosus, mediated at least in part through the interaction of circulating immune complexes with platelet Fc receptors and by promotion of interferon release from plasmacytoid dendritic cells. These findings point to a distinct role for platelets in autoimmunity and support the possibility that platelets are an attractive target in rheumatic disease. Recently, a ground breaking study in Science by Boilard et al., (2010) highlighted that platelets amplify inflammation in arthritis via collagen-dependent microparticle production. Platelet microparticles—submicrometer vesicles elaborated by activated platelets—in joint fluid from patients with rheumatoid arthritis and other forms of inflammatory arthritis, but not in joint fluid from patients with osteoarthritis. Platelet microparticles were proinflammatory, eliciting cytokine responses from synovial fibroblasts via interleukin-1. Consistent with these findings, depletion of platelets attenuated murine inflammatory arthritis. Using both pharmacologic and genetic approaches, the collagen receptor glycoprotein VI was implicated as a key trigger for platelet microparticle generation in arthritis pathophysiology.

Transient receptor potential melastatin 7 (TRPM7) is involved in both normal physiological processes and pathology of various diseases. It is the main target of Magnesium signaling and is involved in Mg import into the cell, while simultaneously exporting Ca2+ions out of the cell. Its cellular expression is increased under hyomagnesic condition via regulation of its conserved motifs on it 5' leader open reading frame. As people tend to become Mg deficient in older age, this is mirrored by a systemic cellular expression of TRPM7 on cells. Increased TRPM7 expression has been linked with cellular dysfunction and disease. A case in point being that the TRPM7 channel functions and contributes to rheumatoid arthritis (RA) by regulating apoptosis and signaling networks in rheumatoid arthritis (RA) fibroblast-like synoviocytes. This provides a compelling paradigm of the direct involvement of Magnesium and its cellular target, TRPM7, in the pathogenesis of RA, and its potential therapeutic use in this inflammatory condition, and in the long-term management of patients with inflammatory joint disease.

Magnesium appears to play a vital function in cardiovascular stability and health, but an optimal dose and formulation has not been defined. Bioavailability of Magnesium alone is a major issue, as different salts have different efficacies in various target cells. Potassium is also a mineral crucial for life, notably necessary for the heart, kidneys, and other organs to work normally. Potassium ions are necessary for the function of all living cells. Potassium ion diffusion is a key mechanism in nerve transmission, and potassium depletion in animals, including humans, results in various cardiac dysfunctions. Calcium is essential for maintaining strong bones and carrying out many important functions such as for muscles to move and for nerves to carry messages between the brain and every part of the body. In addition, calcium is used to help blood vessels move blood throughout the body and to help release hormones and enzymes that affect almost every function in the human body.

A problem is that the current life-style does not enable an adequate intake of dietary minerals and trace elements which are essential nutrients to all living organisms. For example processed foods often lack a sufficient amount of minerals.

It is to be understood that minerals are naturally occurring inorganic elements expressing the same internal structure and characteristic chemical composition, form, and physical properties. In the present application we understand by "minerals" or "chemical elements" the dietary minerals and trace elements that are essential nutrients for mammals and more particularly for humans.

The body water constitutes as much as 73% of the body weight of a newborn infant. At birth, the saline body water is enriched with minerals and elements to aid in our growth, healing, skin health and hair. Mineral levels decrease to approximately 40% with ageing. Other causes of depletion include our lifestyle patterns such as smoking, drinking, medicines etc. Additionally, certain situations cause loss of certain mineral elements faster than they can replace it from your diet. These situations include treatment with "water pills" (diuretics such as furosemide, hydrochlorothiazide), or other medical conditions (e.g., severe diarrhoea/vomiting, stomach/intestinal absorption problems, poorly controlled diabetes).

If prolonged, this depletion in minerals can cause severe deficiencies in the body functions affecting metabolism and cell growth and repair, further leading to major skin, cardiovascular, joint, muscle or nerve disorders.

A proposed solution to this problem consists in an intake of dietary supplements formulated to contain several different chemical elements (as compounds), a combination of vitamins and/or other chemical compounds, or a single element (as a compound or mixture of compounds), such as calcium (as carbonate, citrate, etc.) or magnesium (as oxide, etc.), chromium (usually as picolinate) or iron (as bisglycinate).

Another proposed solution consists in an intake of Nutraceuticals. Nutraceuticals are products derived from food sources that are purported to provide extra health benefits, in addition to the basic nutritional value found in foods.

However, in order to be absorbed by the body in an efficient and effective manner each mineral, vitamin and enzyme requires a co-factor or sometimes referred to as an ion pairing. Vitamin, mineral, protein and enzyme interaction and interdependency is well documented scientifically and recognized. For example, Magnesium competes with fluoride and will decrease absorption of that mineral when taken at the same time.

Therefore there are problems in providing an adequate intake of essential minerals which consists in formulating a balanced mineral composition that allows a good and effective absorption of the minerals in the body and their interaction with vitamins and enzymes.

There is a need for providing a balanced composition of minerals for cosmetic or pharmaceutical, nutraceutical and/or veterinary uses.

It is an aim of the present invention to provide a balanced composition of minerals for cosmetic, pharmaceutical nutraceutical and/or veterinary uses. It is also an aim of the present invention to provide a simple and cost effective solution for supplying an effective amount of essential minerals in a pharmaceutical, cosmetic, nutraceutical and/or veterinary composition.

These and other objects and advantages of the invention will become apparent from the description of the preferred embodiments detailed below.

SUMMARY OF THE INVENTION

According to the invention, there is provided a super-concentrated seawater mineral extract comprising sea minerals in a concentration of at least 20%.

Preferably the seawater mineral extract is derived from seawater having a salinity of from 3.4% to 3.6% Brix.

By seawater minerals it is to be understood that this includes any naturally occurring minerals that may be found or are contained in seawater.

Advantageously, the mineral content of seawater has a high correlation with the composition of human serum. Advantageously seawater contains the complete spectrum of minerals and a perfectly balanced composition of each of the necessary minerals. Advantageously, the super-concentrated seawater mineral extract according to the invention has a low sodium concentration, a high magnesium concentration, and a stable mineral composition. Another advantage is the super-concentrated seawater mineral extract of the present invention is stable for at least up to three years and has a shelf life of up to two years.

Preferably the super-concentrated seawater mineral extract comprises sea minerals in a concentration of in the range of 35% to 47%.

More preferably the super-concentrated seawater mineral extract comprises sea minerals in a concentration of in the range of 35% to 45%.

In a preferred embodiment the sea minerals comprise a magnesium concentration of at least 60 g/L, preferably at least 65 g/L, more preferably between 62 g/L to 76 g/L.

In a preferred embodiment the sea minerals comprise a Sodium concentration of at least 15 g/L, preferably at least 23 g/L, more preferably between 22 g/L to 28 g/L.

In a preferred embodiment the sea minerals comprise a concentration of Potassium of at least 18 g/L, preferably at least 23 g/L, more preferably between 21 g/L to 26 g/L.

In a preferred embodiment the sea minerals comprise a concentration of Boron of at least 0.15 g/L, more preferably between 0.18 g/L and 0.26 g/L.

In a preferred embodiment the sea minerals comprise a concentration of Calcium of at least 0.07 g/L more preferably between 0.075 g/L and 0.09 g/L.

In a preferred embodiment, the sea minerals comprise Magnesium, Sodium, Potassium, Boron, Calcium, Nickel, Copper, Strontium, Molybdenum, Iron, Zinc, Aluminium, Manganese, Barium, Vanadium, Chromium, Arsenic, Antimony, Beryllium, Cobalt, Selenium, Cadmium, Tin, Mercury, Thallium, and Lead.

Advantageously, the super-concentrated seawater mineral extract according to the invention comprises each of the noted twenty minerals and trace elements necessary for human health.

In an embodiment the super-concentrated seawater mineral extract according to the invention is obtained from seawater by electrodialysis or by high-pressure reverse osmosis.

In a preferred embodiment the super-concentrated seawater mineral extract according to the present invention is obtained by a sea water harvesting process including the steps of collecting sea water, filtering the sea water, passing the filtered sea water through a high-pressure reverse osmosis membrane to separate the sea water into desalinated water and concentrated sea water, delivering the concentrated sea water to an evaporator, heating the concentrated sea water in the evaporator under vacuum to produce calcium sulphate, sea salt and super-concentrated sea water from which concentrated seawater mineral extracts are derived.

A second aspect of the invention concerns a nutraceutical composition comprising a super-concentrated seawater mineral extract according to the invention as an active agent.

The nutraceutical composition according to the invention is active in preventing chronic diseases, improving health, delaying the aging process, increasing a person's disease free years and promoting an aging well paradigm.

A third aspect of the invention concerns a pharmaceutical or cosmetic composition comprising a super-concentrated seawater mineral extract according to the invention as an active agent.

In a preferred embodiment, the pharmaceutical or cosmetic composition comprises a super-concentrated seawater mineral extract according to the invention at a concentration in the range of 0.01% to 5%, preferably in the range of 0.2% to 0.5%, more preferably at a concentration of 0.33%.

In a preferred embodiment the composition comprises one or more chelating amino acids. Preferably the chelating amino acids are one or more of Glycine, Lysine or Taurine. More preferably the chelating amino acid is Glycine.

In a preferred embodiment the composition comprises additional active ingredients including vitamins, polyphenols, amino acids, peptides, proteins, carbohydrates, fibre, organic acids, plant extracts, active molecules such as statins and the like.

A fourth aspect of the invention concerns a super-concentrated seawater mineral extract according to the invention alone or in a pharmaceutical composition for use as a medicament.

In a preferred embodiment the invention concerns a super-concentrated seawater mineral extract according to the invention alone or in a pharmaceutical composition for use as an anti-inflammatory agent.

In a preferred embodiment the invention concerns a super-concentrated seawater mineral extract according to the invention alone or in a pharmaceutical composition for use as an active agent for stimulating stem cells and/or the cell production system and/or the production of micro vascular networks.

A fifth aspect of the invention concerns a pharmaceutical composition according to the invention for use in treating and/or preventing cardiovascular disorders.

In a preferred embodiment the pharmaceutical composition comprises a combination of the super-concentrated seawater mineral extract according to the invention with a statin for use in reducing cholesterol levels and/or reducing C-reactive protein levels and/or reducing CIMT and/or to reduce stroke morbidity and mortality.

Another aspect of the invention concerns a pharmaceutical composition according to the invention for use in treating skin disorders.

Another aspect of the invention concerns a pharmaceutical composition according to the invention for use in treating joint disorders.

Another aspect of the invention concerns a pharmaceutical composition according to the invention for use in treating muscle disorders.

Another aspect of the invention concerns a pharmaceutical composition according to the invention for use in treating nerve disorders.

A yet another aspect of the invention concerns a method of hydrating and smoothing a person's skin, consisting of administering to said patient a cosmetic composition according to the invention.

Yet another aspect of the invention concerns a method of stimulating tissue repair of a patient's skin, muscle, joints or nerves in need thereof, consisting of administering to said patient a pharmaceutical composition according to the invention.

Another aspect of the invention concerns a method of treating hair or scalp disorders consisting of administering to a patient a composition according to the invention.

Another embodiment concerns a veterinary composition comprising the super-concentrated seawater mineral extract according to the invention as an active agent for use in the treatment of conditions, disorders, ailments and diseases in animals.

In a preferred embodiment the present invention provides a veterinary composition comprising the seawater mineral extract for use in the treatment of herbivores and ruminants.

In a more preferred embodiment the present invention provides a veterinary composition comprising the seawater mineral extract for use in the treatment of animals belonging to the equus genus.

In a most preferred embodiment the present invention provides a veterinary composition comprising the seawater mineral extract for use in the treatment equines.

Yet another aspect of the invention concerns the use of the super-concentrated seawater mineral extract according to the invention as a re-mineralising agent to re-mineralise purified water after the water has been purified through any water purification process or to enhance spring, mineral or tap water. Preferably the water/a super-concentrated seawater mineral extract ratio is 3000 parts water to 1 part Super concentrated Minerals. In a preferred embodiment, Calcium Sulphate is further added to the purified water in a ratio of 9000 parts water to 1 part Calcium sulphate.

BRIEF DESCRIPTION OF THE DRAWINGS

The invention will be more clearly understood from the following description of some embodiments thereof, given by way of example only, with reference to the accompanying figures, in which.

DETAILED DESCRIPTION OF THE PREFERRED EMBODIMENTS

Figure 1:
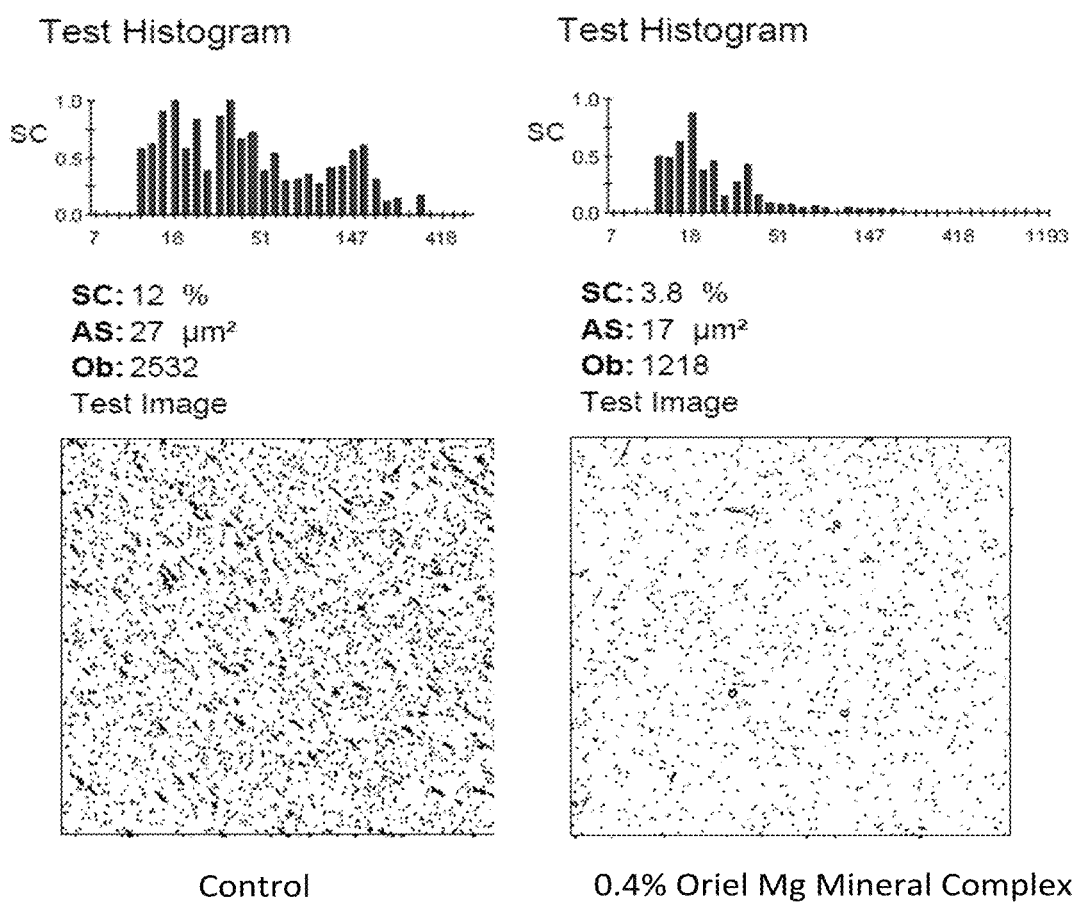
FIG. 1 shows the effects of the seawater mineral extract of the present invention on in vitro platelet inhibition the FIG. 2 shows Platelet activation and P-selectin expression in response to the seawater mineral extract of the present invention.

The present invention provides a super-concentrated seawater mineral extract comprising sea minerals in a concentration of at least 20%.

Sea water salinity is generally defined in parts per thousand (ppt) by weight or Practical Salinity Units (PSU). The index of refraction (or refractive index) is the ratio of the speed of light travelling through a vacuum to the speed of light in the material being tested. In a solution of salt in water the refractive index changes dependent on how much of each component is present.

In this specification the sea minerals concentration is measured in Degrees Brix (° BX) which represents the strength of the solution as percentage by mass, or volumetric mass density taking into account the refractive index.

Therefore a Brix measurement of from 0 to 3.8% Brix corresponds with a seawater salinity measurement of from 0 to 30 parts per thousand (ppt).

The super-concentrated seawater mineral extract of the invention is obtained from harvesting sea minerals directly from seawater in a manner that delivers a balanced ratio of the relevant minerals.

Throughout this specification "seawater" refers to surface seawater, intermediate seawater or deep seawater. The term "seawater" is taken to include the Pelagic environments of the Neritic Province and Oceanic Province and at depths within the Epipelagic (also referred to as Euphotic), Mesopelagic (also referred to as Disphotic), Bathypelagic (also referred to as aphotic) and Abyssopelagic ranges and as such includes brackish water (for example estuaries, mangroves, swamps and brackish seas) with a salinity of from 0.5 to 30 ppt, as well as saline water (sea water) with a salinity of from 30 to 50 ppt. Such "seawater" may include slack water or seawater under the influence of tidal movements, currents, streams and other water flow. Such "seawater" typically having a salinity of around 35 g/kg or 35 ppt, although lower values are typical near coasts where rivers enter the ocean. By "seawater" we do not refer to rivers and lakes or to places where higher salinities are found such as brine water or pools, for example the Dead Sea that has a salinity of more than 200 g/kg or over 50 ppt.

Preferably, seawater with a measured salinity or mineral content of 3.4% to 3.6% is used for harvesting the sea minerals and the seawater mineral extract comprising said sea minerals.

In one embodiment the seawater mineral extract is prepared from seawater harvested from the sublittoral portion of the neritic province of the euphotic zone.

In another embodiment the seawater mineral extract is prepared from seawater harvested from the a euphotic zone that absorbs substantially a mixture of visible blue, green and yellow light, In another embodiment the seawater mineral extract is prepared from seawater harvested at a water depth of between 20 and 30 feet. One advantage to harvesting at a depth of 20 to 30 feet is that the harvesting method remains inexpensive and ease of access to maintain equipment.

In another embodiment the seawater mineral extract is prepared from seawater harvested from the Irish Sea.

In one embodiment seawater harvested from the bay of Port Oriel, Clogherhead, Drogheda, County Louth, Ireland and the surrounding littoral zone, sublittoral zone or coastal areas may be used in the preparation of the seawater extract. The bay of Port Oriel is situated on the northwest side of the headland of Clogher Head that protrudes directly out into deep water straits and extends towards Dunany Point.

In another embodiment the specific demarcated seawater harvesting area stretches from the Southernmost tip of Clogher Head with Latitude=53.79497 (north), Longitude=- 6.21778 (west), Latitude=53°47'42" (north), Longitude=6°134" (west) to the Northern tip of Dunany Point Latitude=53.86144 (north), Longitude=-6.23838 (west), Latitude=53°51'41" (north), Longitude=6°14'18" (west).

In another embodiment the seawater extract is prepared from seawater harvested from the bay of Port Oriel where the Gulf Stream meets the massive outflow of the River Boyne.

Advantageously, sea water from the bay of Port Oriel has been regularly tested by the Marine Institute of Ireland and approved as international "Grade "A" Shellfish Quality" the purest of the sea. Additionally these sea waters have a high saline and mineral content due to the powerful deep water currents flowing from the cold depth of the North Atlantic. Furthermore the Gulf stream, tidal movements and the outflow of the River Boyne, create an environment unique to the Bay of Port Oriel and contribute to the unique mineral composition of the seawater mineral extract of the present invention and in particular to the high saline and mineral content. The water at the bay of Port Oriel has been consistently tested at a density 3.5%-3.6% Brix.

Such unique conditions have been recognised and as such the salt and "seawater" extracts harvested from this location have been awarded Protected Designation of Origin (PDO) status.

The super-concentrated seawater mineral extract according to the invention can be obtained from seawater by electrodialysis or by high-pressure reverse osmosis.

In a preferred embodiment, the super-concentrated seawater mineral extract according to the present invention is obtained by a sea water harvesting process including the steps of collecting sea water, filtering the sea water, passing the filtered sea water through a high-pressure reverse osmosis membrane to separate the sea water into desalinated water and concentrated sea water, delivering the concentrated sea water to an evaporator, heating the concentrated sea water in the evaporator under vacuum to produce calcium sulphate, sea salt and a super-concentrated seawater mineral extract comprising sea minerals in a concentration of at least 20%.

In an embodiment, between 40% and 75% of the total level of sodium is removed from the collected sea water during the evaporation process depending on the harvesting conditions and the tidal flows at different times of year.

In an embodiment, between 45%-75% of the total level of Calcium Sulphate is removed during the evaporation process, prior to harvesting the minerals.

In a preferred embodiment, the super-concentrated seawater mineral extract is obtained by the sea-harvesting process disclosed in the International Patent Application No. PCT/EP2014/078878 whose content is herein incorporated by reference, wherein the super-concentrated seawater mineral extract according to the invention corresponds to the "super-concentrated sea water" or the "concentrated sea minerals liquor".

Preferably the super-concentrated seawater mineral extract comprises sea minerals in a concentration in the range of 37% to 47%.

The super-concentrated seawater mineral extract is in the form of a concentrated liquid ionized composition which contains a complete spectrum of the essential minerals in ratios that optimize the ability of each mineral to be absorbed, act as co-factor with the multitude of vitamins and/or enzymes and participate in ion pairings within the body.

Advantageously the ionised or ionic liquid form of the composition enables greater bioavailability of the minerals and improved delivery of other key nutrients or active ingredients such as vitamins and/or enzymes.

Dependent on the time of year harvested, the super-concentrated seawater mineral extract of the invention can have a 10% variation of the concentration of each mineral and a variance of 5% of the ratio of these minerals.

In a preferred embodiment, the sea minerals comprise a magnesium concentration of at least 60 g/L, preferably at least 65 g/L, more preferably between 62 g/L to 76 g/L, more preferably still from 76 g/L to 99 g/L and most preferred from 76 g/L to 90 g/L.

One advantage is that Magnesium is a mineral that's crucial to the body's function. It is one of the building blocks that are required for more than six hundred biochemical and enzymatic reactions in the body. Magnesium helps keep blood pressure normal, bones strong, the heart rhythm steady, the transmission of nerve impulses, body temperature regulation and detoxification and energy production. It plays a crucial role in the repair and regeneration of cell tissue while it is a key mineral for the health and formation of bones and teeth as it is necessary for the efficient absorption of calcium.

In a preferred embodiment, the sea minerals comprise a Sodium concentration of at least 15 g/L, preferably at least 23 g/L, more preferably between 22 g/L to 28 g/L.

In a preferred embodiment, the sea minerals comprise a concentration of Potassium of at least 18 g/L, preferably at least 23 g/L, more preferably between 21 g/L to 26 g/L.

In a preferred embodiment, the sea minerals comprise a concentration of Boron of at least 0.15 g/L, preferably at least 0.18 g/L, more preferably between 0.20 g/L to 0.25 g/L.

In a preferred embodiment, the sea minerals comprise a concentration of Calcium of at least 0.07 g/L preferably at least 0.075 g/L, more preferably between 0.070 g/L to 0.087 g/L.

In a preferred embodiment, the sea minerals comprise Magnesium in a concentration between 62 g/L to 95 g/L, Sodium in a concentration between 22 g/L to 28 g/L, Potassium in a concentration between 21 g/L to 26 g/L, Boron in a concentration between 0.20 g/L to 0.23 g/L, and Calcium in a concentration between 0.070 g/L to 0.087 g/L.

In a preferred embodiment, the mineral salt content further comprises trace elements formed of one or more of nickel, copper, strontium, molybdenum, iron, zinc, aluminium, manganese, barium, vanadium, chromium, arsenic, antimony, beryllium, cobalt, selenium, cadmium, tin, mercury, thallium and lead.

One advantage is the balance achieved between the key minerals and trace elements, acting as co-factors, provides excellent bioavailability of the all the minerals and trace elements, and in particular optimises the delivery of Magnesium, than if they were applied or consumed separately as singular minerals or elements.

A second aspect of the invention concerns a nutraceutical composition comprising a super-concentrated seawater mineral extract according to the invention as an active agent.

Nutraceuticals are products derived from food sources that are purported to provide extra health benefits, in addition to the basic nutritional value found in foods. The nutraceutical composition of the invention can be any nutraceutical formulation known by the person skilled in the art such as dietary supplements, and may be in forms such as tablets, capsules, soft gels, gel caps, liquids, or powders or as functional foods. They may also support the structure or function of the body, and are often used in recovery post exercise and training. Reports in peer reviewed international scientific and medical journals have compounded the role of Magnesium in all of these aspects.

The nutraceutical composition according to the invention is active in preventing chronic diseases, improving health, delaying the aging process, increasing a person's disease free years and promoting an aging well paradigm.

A third aspect of the invention concerns a pharmaceutical or cosmetic composition comprising a super-concentrated seawater mineral extract according to the invention as an active agent.

In a preferred embodiment, the composition comprises Glycine as a chelating amino acid.

The super-concentrated seawater mineral extract of the invention may be solubilized in one or more solvents conventionally used by those skilled in the art, such as water, glycerol, ethanol, propylene glycol, butylene glycol, dipropylene glycol, ethoxylated or propoxylated diglycols, cyclic polyols, vaseline, petroleum jelly, vegetable oil or any mixture of these solvents. Preferably the super-concentrated seawater mineral extract is added to, and solubilised in, glycerol where the super-concentrated seawater mineral extract is added at a concentration from 3% to 10%. Typically, glycerol or any other conventional solvent may be used in a concentration in the range of 90% to 97%.

In a preferred embodiment, the composition comprises additional active ingredients including vitamins, polyphenols, amino acids, peptides, proteins, carbohydrates, fibre, organic acids, plant extracts, active molecules such as statins and the like.

In a preferred embodiment the composition can be formulated as capsule, intravenous composition, tablet, gel, encapsulated, cream, gel, spray or any other recognized manner of introducing minerals to the body.

Preferably the composition according to the invention may be topically applied, more preferably the composition is in the form of a gel or a cream. Advantageously this administration form demonstrates excellent transdermal abilities in the effectiveness of mineral absorption by the skin.

In a preferred embodiment the composition can be formulated as a Nutraceutical composition. Preferably, the composition is administered as drops in any liquid such as water, juice etc. Advantageously due to the ionic form of the super-concentrated sea minerals extract the minerals are rapidly absorbed when taken in this way.

A fourth aspect of the invention concerns a super-concentrated seawater mineral extract according to the invention alone or in a pharmaceutical composition for use as a medicament.

In a preferred embodiment the invention concerns a super-concentrated seawater mineral extract according to the invention alone or in a pharmaceutical composition for use as an anti-inflammatory agent.

In a preferred embodiment the invention concerns a super-concentrated seawater mineral extract according to the invention alone or in a pharmaceutical composition for use as an active agent for stimulating stem cells and/or the cell production system and/or the production of micro vascular networks.

A fifth aspect of the invention concerns a pharmaceutical composition according to the invention for use in treating and/or preventing cardiovascular disorders.

Throughout this specification "cardiovascular and metyabolic disorders" refers to a class of diseases that involve the heart or blood vessels including ischemic heart disease (IHD), stroke, hypertensive heart disease, rheumatic heart disease (RHD), aortic aneurysms, cardiomyopathy, atrial fibrillation, congenital heart disease, endocarditis, and peripheral artery disease (PAD), cardiovascular disease, carotid intima media thickness (CIMT), hypertension (HTN), Diabetes and Metabolic Syndrome among others.

The pharmaceutical composition according to the invention comprises a super-concentrated seawater mineral extract that includes an optimal level of Magnesium and a formulation that allows an optimal bio-availability and bio-activity of Magnesium. Magnesium is a ubiquitous element, being the fourth most abundant cation in the human body. It is involved in several essential physiological, biochemical, and cellular processes regulating cardiovascular function as well as the development and progression of many chronic illnesses. It plays a critical role in modulating vascular smooth muscle tone, endothelial cell function, and myocardial excitability and is thus central to the pathogenesis of several cardiovascular disorders such as hypertension, atherosclerosis, coronary artery disease, congestive heart failure, and cardiac arrhythmias. More recently, it has been linked to associated conditions such as kidney disease, neurovascular inflammation, platelet activation (thrombosis) and cancer. The extract according to the invention has a molecular and cellular effect on (i) platelets, (ii) endothelial cells and (iii) vascular smooth muscle cells.

The pharmaceutical composition according to the invention has vasodilatory, anti-inflammatory, anti-ischemic, and antiarrhythmic properties. The pharmaceutical composition according to the invention is efficient in the prevention, management and treatment of cardiovascular disease and related chronic disorders.

In a preferred embodiment the pharmaceutical composition comprises a combination of the super-concentrated seawater mineral extract according to the invention with a statin for use in reducing cholesterol levels and/or reducing C-reactive protein levels and/or reducing CIMT and/or to reduce stroke morbidity and mortality.

Another aspect of the invention concerns a pharmaceutical composition according to the invention for use in treating skin disorders.

Throughout this specification "skin disorders" refers to disorders such as irritated, clogged, or inflamed skin with symptoms such as redness, swelling, burning, and itching. Skin disorders include for example Psoriasis, Dermatitis, Athletes Foot, Eczema, Acne, Rosacea, Skin Cancers, Skin rashes, Skin Allergies, Diaper rash, Insect bites and stings, Fungal infections, Impetigo, Shingles, Scabies, Scar repair.

Another aspect of the invention concerns a pharmaceutical composition according to the invention for use in treating joint disorders.

It will be understood that "joint disorders" refers to multiple Joint disorders such as injury from overuse, infection, an immune system launching a misplaced attack, or degeneration including for example Osteoarthritis, Dislocation, Sprains, Bursitis, Arthritis, Rheumatoid Arthritis (RA), Gout, Lyme Arthritis.

Through accessing the skin layers and the circulatory system in the manner described the minerals coupled with the chosen amino acid re-activate the communication network of the various cells. In turn promoting the re-activation of these cells to reduce inflammation, swelling, stiffness and pain through the production of healthy cells which in turn promote the production of healthy tissue which allows movement and reduction in pain.

Another aspect of the invention concerns a pharmaceutical composition according to the invention for use in treating muscle disorders.

It will be understood that "muscle disorders" refers to muscle injury or overuse, such as sprains or strains, cramps or tendinitis, electrolyte depletion, muscle wastage, muscle cramps, tics, twitches, genetic disorders, such as Muscular dystrophy, some cancers, muscle inflammation, such as Myositis, infections.

Another aspect of the invention concerns a pharmaceutical composition according to the invention for use in treating nerve disorders.

It will be understood that "nerve disorders" refers to is vulnerable to various disorders of the nervous system such as trauma, infections, degeneration, structural defects, tumours, blood flow disruption, autoimmune disorders, including Neurosis, post-surgery applications, Nerve related pain, Vascular disorders, such as stroke, transient ischemic attack (TIA), subarachnoid hemorrhage, subdural hemorrhage and hematoma, and extradural haemorrhage; Infections, such as meningitis, encephalitis, polio, and epidural abscess; Structural disorders, such as brain or spinal cord injury, Bell's palsy, cervical spondylosis, carpal tunnel syndrome, brain or spinal cord tumors, peripheral neuropathy, and Guillain-Barré syndrome; Functional disorders, such as headache, epilepsy, dizziness, and neuralgia; Degeneration, such as Parkinson's disease, multiple sclerosis, amyotrophic lateral sclerosis (ALS), Huntington's chorea, and Alzheimer's disease.

A yet another aspect of the invention concerns a method of stimulating tissue repair of a patient's skin, muscle, joints or nerves in need thereof, consisting of administering to said patient a pharmaceutical composition according to the invention.

A yet another aspect of the invention concerns the use of magnesium in the management and treatment of psychological disorders such as chronic stress, insomnia, post traumatic stress, depression, anxiety, borderline personality disorder and bi-polar consisting of administering to said patient a pharmaceutical composition according to the invention A yet another aspect of the invention concerns the use of magnesium in the management and treatment of conditions such as Autism, It will be understood that "tissue repair" includes but is not limited to wound healing, prevention and amelioration of scar tissue formation and tissue damage, such as burns, cuts, grazes and any other form of dermal abrasion.

Yet another aspect of the invention concerns a method of hydrating and smoothing a person's skin, consisting of administering to said patient a cosmetic composition according to the invention.

The cosmetic composition according to the invention is effective in hydrating, smoothing, revitalising, and rejuvenating the skin. The cosmetic composition according to the invention improves significantly the skin's appearance, quality and radiance. Furthermore the cosmetic composition according to the invention prevents or treats the signs of skin aging.

Another aspect of the invention concerns a method of treating hair and scalp disorders consisting of administering to a patient a composition according to the invention.

It will be understood that "hair and scalp disorders" refers to multiple hair loss and scalp disorders including for example Hair Loss, Alopecia, effects of radium, or chemotherapy treatments.

Through accessing the skin layers and the circulatory system in the manner described the minerals coupled with the chosen amino acid re activate the communication network of the scalp and hair follicle cells. In turn promoting the re-activation of same to encourage blood flow back to the point of necessity.

Other features and advantages of the invention will become apparent on reading the following examples given for illustrative purpose and not restrictive.

EXAMPLES

Example 1

Method for Producing a Super Concentrated Seawater Mineral Extract Comprising Sea Minerals in a Concentration of at Least 20%

Sea water is pumped from the sea by a submersible pump through a filtration system into one or more raw sea water storage tanks wherein it is allowed to settle.

The sea water is then pumped from a sea water storage tank into a pre-treatment tank and from there it is filtered and pumped at a pressure of about 900 psi (60 bar) to a high pressure reverse osmosis system. In passing through the high pressure reverse osmosis system the raw sea water is separated into desalinated water which is collected in an interval tank and concentrated sea water which is collected in a concentrated sea water tank. The concentrated sea water is concentrated by approximately 100% to a density of approximately 6-10% i.e. having a salt/mineral content of approximately 6-10%.

From the reverse osmosis system there are two outputs, namely for concentrated sea water and desalinated sea water.

The processing of the concentrated sea water (Approximate Density 6-10%) is as follows. The raw sea water is pumped from the pre-treatment tank to an ultra-filtration (UF) membrane (which is located within the reverse osmosis system). From the UF membrane the sea water is pumped to high pressure reverse osmosis membranes. In passing through the high pressure reverse osmosis membranes the sea water is separated into desalinated water and concentrated sea water. Desalinated water is collected in the interval tank. The concentrated sea water is sent to the concentrated sea water storage tank. From here it is pumped as required to an evaporator, A batch of concentrated sea water (6-10%) is pumped into the evaporator from the concentrated sea water tank. Once the concentrated sea water enters the evaporator it is subjected to a temperature in the range of 55-65° C., preferably about 60° C., and to a vacuum pressure of about 0.8 bar (Gauge value). This results in the separation of the sea water over a period of 12-24 hours in the following manner.

From the evaporator there are three outputs, namely a calcium sulphate outlet, a super-concentrated sea water outlet and a sea salt outlet.

The first part of the output from the evaporator process is calcium sulphate. This is pumped to a calcium settling device in the form of a mixture of calcium sulphate and super-concentrated sea water to allow it to flow at a density of approximately 25%. In the calcium settling device calcium sulphate is separated from the super-concentrated sea water. After separation in the calcium settling device, the super-concentrated sea water is moved to a super-concentrated sea water tank.

The remaining calcium sulphate is now in a thick white semi solid/semi liquid and it is released out through a release valve at the base of the calcium settling device into a separate container.

When the calcium sulphate is left to settle it will become almost solid like with a clear liquid on top of it. This clear liquid is super-concentrated sea water. However when this solution is agitated and stirred it becomes slurry like. The calcium sulphate is now approximately 50% calcium sulphate and 50% Super-Concentrated Sea Water.

The Super-Concentrated Sea Water is now concentrated at approximately 23%-27% density and it represents about 75% of the total contents (salt and Super-Concentrated Sea Water) of the evaporator after extraction of calcium sulphate.

The Sea Salt is now in a form of slurry which will leave the evaporator as a mix of salt and super-concentrated sea water. It represents approximately 50% of the total contents of the evaporator (the total contents inside evaporator is now salt and Super-Concentrated Sea Water). This slurry is pumped into a centrifuge. As the slurry is processed through the centrifuge the Super-Concentrated Sea Water is removed. The salt leaves the centrifuge as a powder salt which is now ready for a roaster.

The centrifuge is used to separate the sea salt and the Super-Concentrated Sea Water which has been pumped from the evaporator. It does this through a rapid turning of the interior barrels which causes the Super-Concentrated Sea Water to separate and the sea salt to be forced against the outer casing and then extracted. The sea salt extracted from the centrifuge is in a powder form (damp particles). The Super Concentrated Sea Water discharged from the centrifuge may be delivered to the Super Concentrated Sea Water tank via return line.

The Super Concentrated Sea Water constitutes a first form of a Super-Concentrated SeaWater mineral extract according to the invention having an Approximate Density of 25%.

Example 2

Method for Producing a Super Concentrated Seawater Mineral Extract Comprising Sea Minerals in a Concentration of in the Range 37% to 47%

A Super Concentrated Sea Water according to Example 2 is produced by the same process as Example 1 and stored in the Super Concentrated Sea Water tank.

Then further steps are carried out to produce a concentrated sea minerals liquor in a concentrated sea mineral capsule. The super-concentrated sea water is pumped to the concentrated sea mineral capsule at a density of approximately 25% from the Super-Concentrated Sea Water tank. In the concentrated sea mineral capsule the Super-Concentrated Sea Water is subjected to a temperature in excess of 100° C. to separate out the majority of the remaining salt in the Super-Concentrated Sea Water to produce a concentrated sea minerals liquor having a density in the range 35% to 47% depending on the required use.

Once produced the concentrated sea minerals liquor is pumped to the concentrated sea minerals tank. Flake salt produced as a by-product of this part of the process is also removed for packing.

The resultant super concentrated sea liquor having an approximate Density in the range 35% to 47% constitutes a second form of a super-concentrated seawater mineral extract according to the invention.

Example 3

Mineral Composition of the Super-Concentrated Seawater Mineral Extract

The super-concentrated seawater mineral extract according to the invention is in a liquid form, as a clear, slightly brown or yellow liquor due to the mineral content.

The seawater mineral extract is rich in elemental and ionised magnesium with significant levels of elemental and ionised Potassium, Calcium and Chloride also present. The extract has no odour due to the extensive purification process while its texture is almost oily yet there is no oil present. It is best described as a lubricating texture that feels pleasant on the skin. This concentrated blend of sea minerals contains the full spectrum of sea minerals, in optimal concentrations and formulation for absorption by the human body.

TABLE 1

Example of mineral composition of the super-concentrated seawater mineral extract obtained from the process as described in Examples 1 and 2.

| Symbol | Mineral | Measure | Screen | Result |
|---|---|---|---|---|
| Mg | Magnesium | mg/L | ICP-MS | 68969.30 |
| Na | Sodium | mg/L | ICP-MS | 27975.50 |
| k | Potassium | mg/L | ICP-MS | 23245.30 |
| B | Boron | mg/L | ICP-MS | 217.41 |
| Ca | Calcium | mg/L | ICP-MS | 78.63 |
| Ni | Nickel | mg/L | ICP-MS | 2.52 |
| Cu | Copper | mg/L | ICP-MS | 1.73 |
| Sr | Strontium | mg/L | ICP-MS | 1.33 |
| Mo | Molybdenum | mg/L | ICP-MS | 0.53 |
| Fe | Iron | mg/L | ICP-MS | 0.53 |
| Zn | Zinc | mg/L | ICP-MS | <0.50 |
| Al | Aluminium | mg/L | ICP-MS | <0.50 |
| Mn | Manganese | mg/L | ICP-MS | 0.23 |
| Ba | Barium | mg/L | ICP-MS | 0.17 |
| V | Vanadium | mg/L | ICP-MS | 0.04 |
| Cr | Chromium | mg/L | ICP-MS | 0.03 |
| As | Arsenic | mg/L | ICP-MS | 0.02 |
| Sb | Antimony | mg/L | ICP-MS | 0.02 |
| Be | Beryllium | mg/L | ICP-MS | <0.005 |
| Co | Cobalt | mg/L | ICP-MS | <0.005 |
| Se | Selenium | mg/L | ICP-MS | <0.005 |
| Cd | Cadmium | mg/L | ICP-MS | <0.005 |
| Sn | Tin | mg/L | ICP-MS | <0.005 |
| Hg | Mercury | mg/L | ICP-MS | <0.005 |
| Tl | Thallium | mg/L | ICP-MS | <0.005 |
| Pb | Lead | mg/L | ICP-MS | <0.005 |

Example 4

Gel Composition Comprising Super-Concentrated Seawater Mineral Extract

Below is provided a typical gel composition comprising the seawater mineral extract having a mineral composition as per Example 3. It is to be understood that the composition is provided by way of example only and should not be read to limit the invention in any way.

TABLE 2

Example of gel composition ingredient list comprising the seawater mineral extract of the present invention.

| INCI Name | Function | Concentration (% w/w) |
| --- | --- | --- |
| Aqua | Solvent | 82.87 |
| Glycine | Skin Conditioning | 0.5 |
| Carbomer | Thickener | 1 |
| Propanediol | Solvent/Viscosity controlling | 4.5 |
| Glycerin | Humectant | 10 |
| Sea Water Extract | Marine Extract | 0.33 |
| Phenoxyethanol | Preservative | 0.8 |

Example 5

Cream Composition Comprising Super-Concentrated Seawater Mineral Extract

Below is provided a typical cream composition comprising the seawater mineral extract having a mineral composition as per Example 3. It is to be understood that the composition is provided by way of example only and should not be read to limit the invention in any way.

TABLE 3

Example of gel composition ingredient list comprising the seawater mineral extract of the present invention.

| Ingredient | Concentration (% w/w) |
| --- | --- |
| Aqua | QS |
| *Helianthus annuus* (Sunflower) Seed Oil | 6 |
| Glycerin | 3.5 |
| *Oenothera Biennis* (Evening Primrose) Oil | 3 |
| Cetearyl Alcohol | 2.14 |
| *Simmondsia Chinensis* (Jojoba) Seed Oil | 2 |
| *Persea Gratissima* (Avocado) Oil | 2 |
| *Theobroma Cacao* (Cocoa) Seed Butter | 1 |
| Tricaprylin | 1 |
| Squalane | 1 |
| Phenoxyethanol | 0.8 |
| Glyceryl Stearate | 0.75 |
| PEG-100 Stearate | 0.75 |
| *Butyrospermum Parkii* (Shea) Butter | 0.5 |
| Carbomer | 0.4 |
| PEG-20 Stearate | 0.36 |
| Sea Water Extract | 0.33 |
| Parfum | 0.3 |
| Hyalauronic Acid | 0.01 |
| Ascorbic Acid | 0.01 |
| Tocopherol | 0.01 |
| Benzyl Salicylate | 0.0192 |
| Citronellol | 0.00146 |
| Geraniol | 0.00246 |
| Alpha-Isomethyl Ionane | 0.00756 |

Example 6

Bioavailability

Preliminary data points to the fact that the seawater mineral extract is both bioavailable and bioactive. Initial findings suggest that the seawater mineral extract is a highly efficient source of magnesium that is readily taken up by the cells via a family of magnesium transporters such as the 'Chanzyme', TRPM7 and MagT1, CNNM3, TRPM6, SLC41 and MRS2.

The seawater mineral extract has been observed to be in the bloodstream, intracellular and producing significant positive and functional benefits in less than 90 mins.

This is most likely due to the mineral composition of the seawater mineral extract comprising minerals in their ionized form. Sometimes also referred to as "Free Form"

Example 7

Platelets Activation and p-Selectin Expression

Effects of the seawater mineral extract on p-selectin positive platelet micro-particles were measured using a standard flow cytometer. Whole blood samples were collected before and after an oral composition comprising the seawater mineral extract of the present invention. Resting platelets and untreated platelets were used as negative control. Changes in CD62P+ Platelet Microparticle (PMP) formation (green fluorescence logarithmic scale) were then recorded using a shear stress activation procedure with the IMPACT-R analyser—which is indicative of a reduction of coagulation and inflammation potential.

Figure 2:
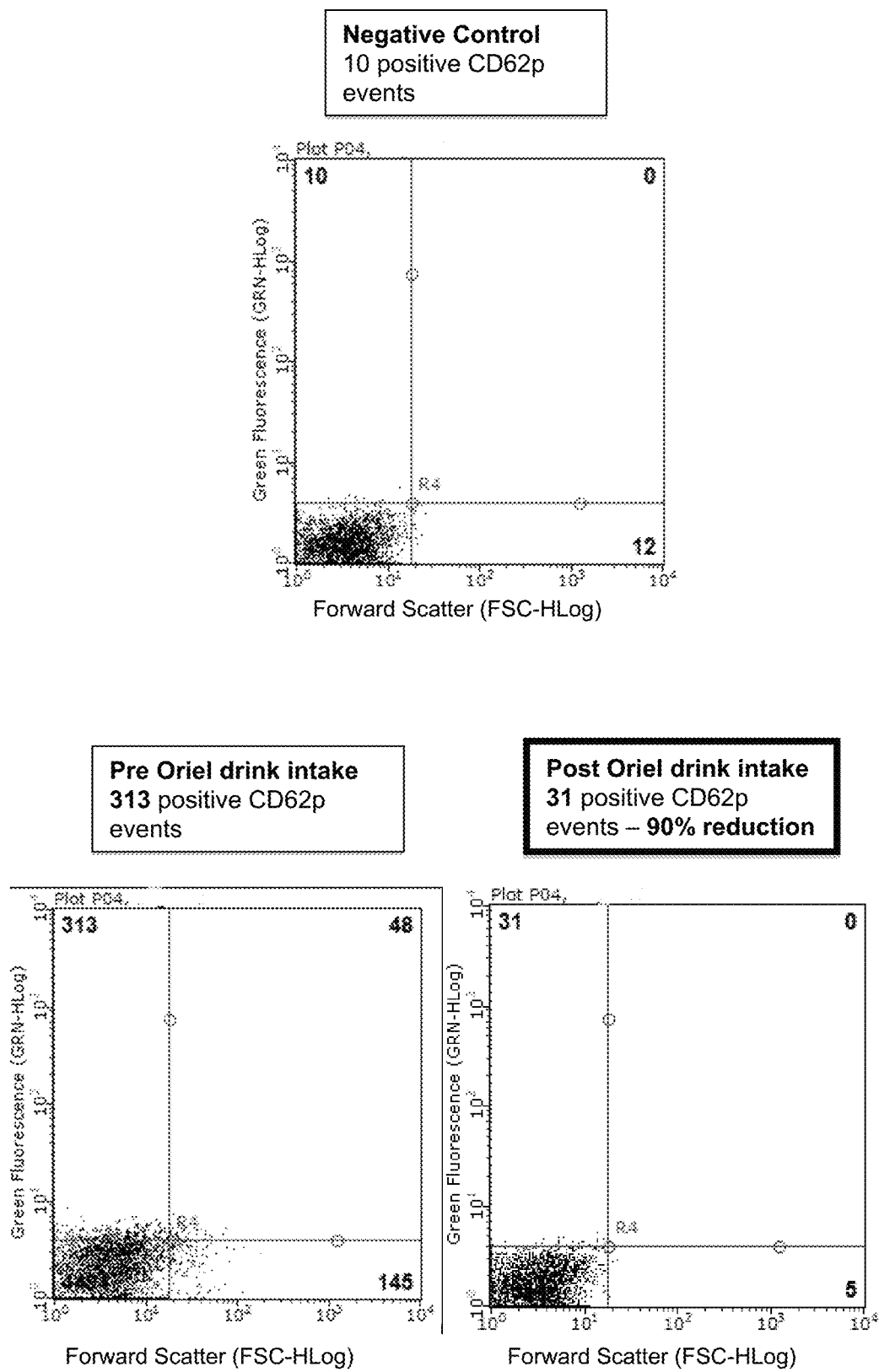

Results are shown in FIG. 2. Negative control showed 10 positive CD62p events. Pre-intake of the seawater mineral extract of the present invention, 313 positive CD62p events were recorded. Post-intake of the seawater mineral extract of the present invention, a profound change in CD62P+ Platelet Microparticle (PMP) formation was observed with 31 positive CD62p events recorded.

Findings indicate that the seawater mineral extract of the present invention reduces p-selectin expressing microparticles indicative of platelet activation by 90%.

Example 8

Magnesium Signalling in Platelets and Platelet Microparticles (MPs)

The seawater mineral extract was administered orally and platelet analysis was performed before and after administration using a shear dependent whole blood assay-IMPACT-R. Platelet adhesion is denoted by SC-surface coverage and platelet aggregation is denoted by AS-aggregated size.

Treatment of platelets with the seawater mineral extract in vitro inhibits platelet adhesion by over 50% while reducing platelet aggregation by approximately 40%, as shown in FIG. 1. In particular inhibition of platelet activation, specifically platelet aggregation was reduced from 27 to 17%.

In vitro studies demonstrate that treatment of whole blood ex vivo using various concentrations of the seawater mineral extract inhibits platelet activation, specifically adhesion.

Example 9

NFκB Gene Regulation

Human primary cells (dermal fibroblasts and human aotic endothelial cells) were treated with various concentrations of the seawater mineral extract and then inflamed. The cells were harvested and, using $RT^2$-qPCR focused arrays, the expression of genes involved in the NFκB signalling pathway were investigated.

Down regulation of genes involved in the NFκB signalling pathway were observed demonstrating both a cytoprotective and anti-inflammatory effect of the seawater mineral extract.

Example 10

PPARγ Gene Regulation

Human primary cells (dermal fibroblasts and human aotic endothelial cells) were treated with various concentrations of the seawater mineral extract and then inflamed. The cells were harvested and, using $RT^2$-qPCR focused arrays, the expression of genes involved in the PPARγ signalling pathway were investigated.

Up-regulation of genes involved in the PPARγ signalling pathway were observed demonstrating both a cytoprotective and anti-inflammatory effect of the "seawater" extract.

Example 11

Biocompatibility Study

Real-Time Cellular analysis was carried out on Primary Human Dermal Keratinocytes.

Figure 3:
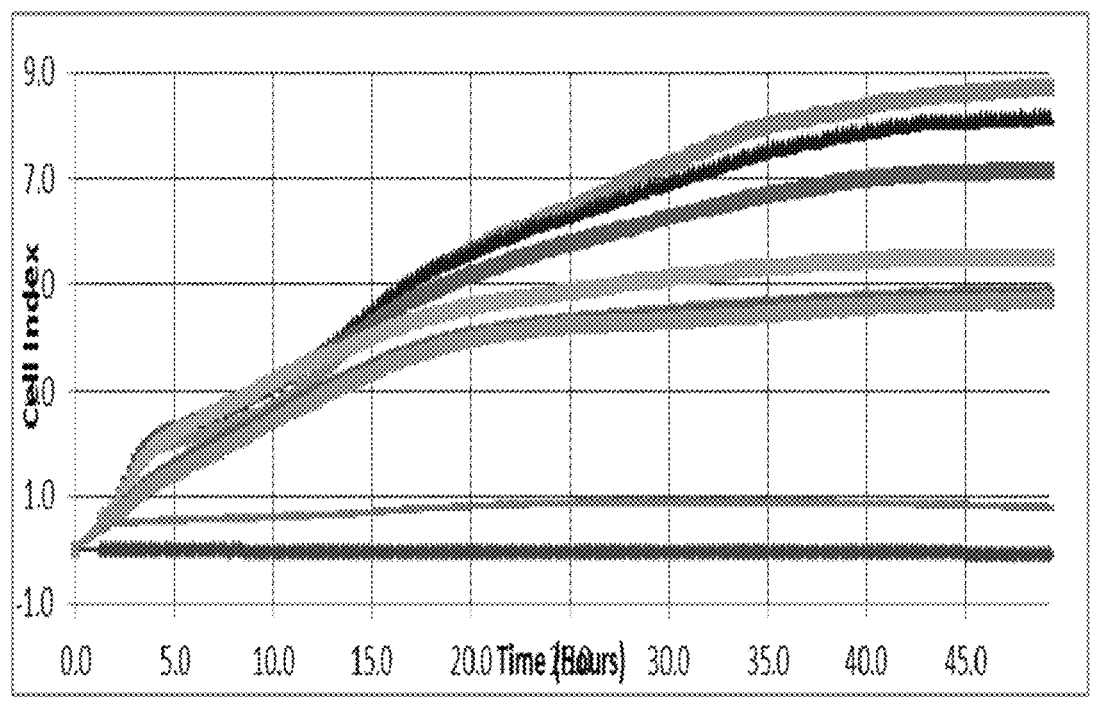
FIG. 3 shows Real-Time Cellular response of Primary Human Dermal Keratinocytes to the seawater mineral extract of the present invention.
Figure 3:
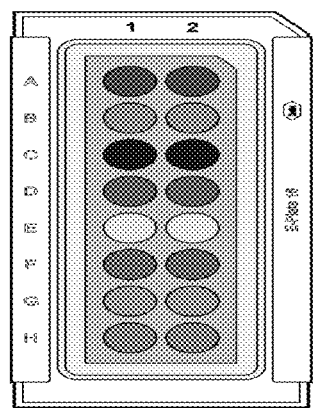

Cell were grown on a 2.5-Dimensional Extra Cellular Matrix environment as a model of skin tissue, to which varying concentrations of the seawater mineral extract (0.1% to 1.5%) were added with measurements being taken over a period of four days (FIG. 3). Cellular tolerance (assessed by impedance), cytotoxicity, and cellular response with respect to the compound kinetics and dynamics were determined.

Primary overall analysis over the 4 day study highlight that, the seawater mineral extract is highly biocompatible and well tolerated up to concentrations of 1%.

No apoptosis or cell death was observed, however cellular dynamics were arrested at concentrations close to 1.5%, i.e. the cells adhered and survived but did not spread, integrate into the Extracellular Matrix or proliferate but were held in cell cycle arrest (FIG. 3).

Long term exposure studies highlighted one potential beneficial effect of the seawater mineral extract on keratinocyte cell biology in that it appreciably slowed the rate of keratinocyte cell proliferation up to concentrations of 0.8%, without inhibiting the process (especially at concentrations between 0.1% to 0.4%).

Example 12

Real Time Adhesion of Primary Human Dermal Keratinocytes

Real-Time Cellular analysis was carried out on two of the major skin cell types, Primary Human Dermal Fibroblasts and Primary Human Dermal Keratinocytes.

Cell were grown on a 2.5-Dimensional Extra Cellular Matrix environment as a model of skin tissue, to which varying concentrations of the seawater mineral extract (0.1% to 1.5%) were added with measurements being taken over a period of 2-3 hours.

Temporal analysis, along the time axis (FIG. 4), facilitated functional studies in relation to a number of cell fate and functions, such parameters are important for skin health. These included (1) cell adhesion, (2) cell activation and spreading, (3) cell proliferation or cell quiescence and (4) apoptosis/cytotoxicity.

Figure 4:
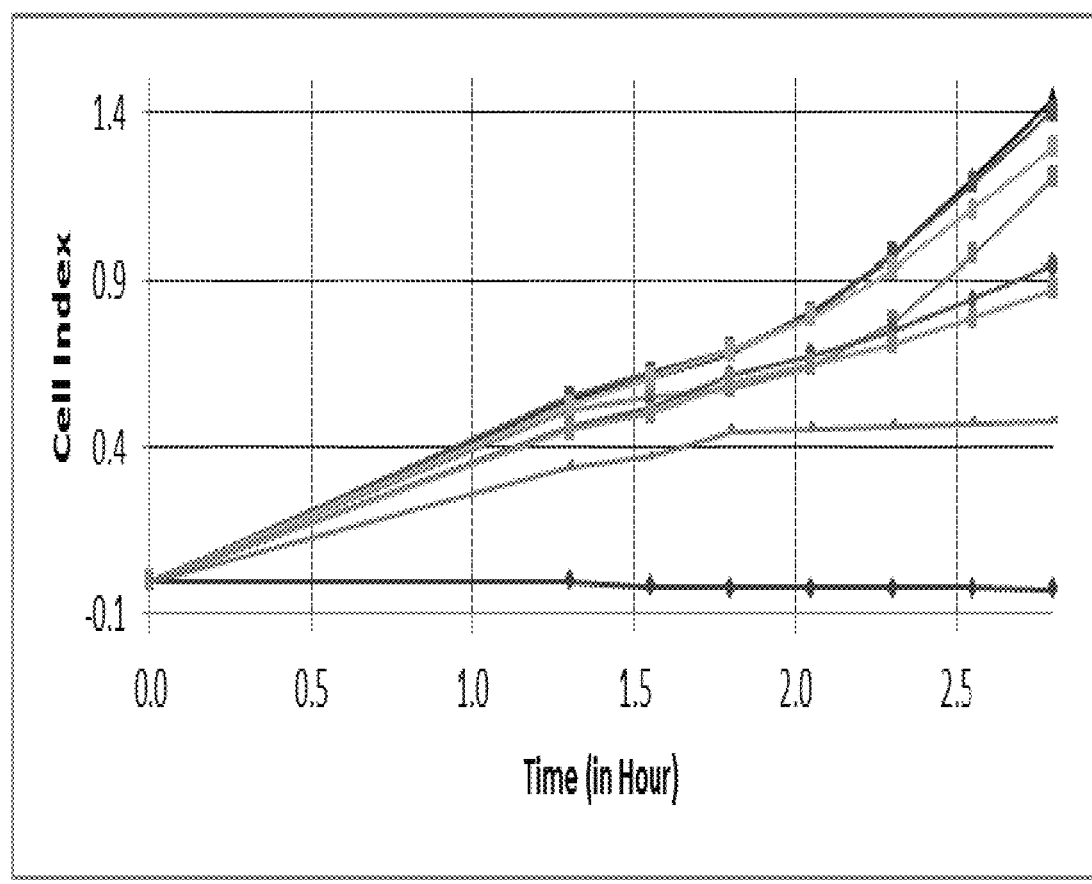
FIG. 4 shows Real-Time Cellular Adhesion of Primary Human Dermal Keratinocytes, in response to the seawater mineral extract of the present invention.
Figure 4:
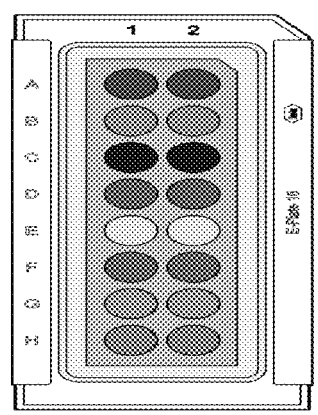

Cellular adhesion dynamics, mediated through Keratinoctye integrin receptors, to the Extra Cellular Matrix environment are demonstrated (FIG. 4). From these cellular kinetics and dynamics it is shown that the seawater mineral extract promotes cell adhesion at three concentrations—0.1%, 0.2% and 0.4%. At these concentrations its increases the rate of cell adhesion, as demonstrated by the increase in line slope, and also the final cell spreading, as indicated by the greater Cell Index (CI) at 2 hours 45 minutes.

The implications of these findings are that the seawater mineral extract has the potential to improved skin tone and biomechanics by increasing and improving the biological process known as Cellular Tensegrity.

Concentrations of the seawater mineral extract at 1.5% greatly reduces the rate of adhesion and cell spreading, but does not reduce cell viability.

Concentrations of the seawater mineral extract at both 0.6% and 0.8%, modestly reduce cell spreading when compared to control keratinocytes (media and cells only), but does has no effect on cell adhesion dynamics and kinetics (i.e. formation of Focal Contacts, Focal Complexes and Focal Adhesions) when compared to control.

Example 13

Real Time Adhesion Dynamics of Primary Human Dermal Keratinocytes

Real-Time Cellular analysis was carried out on Primary Human Dermal Keratinocytes.

Cell were grown on a 2.5-Dimensional Extra Cellular Matrix environment as a model of skin tissue, to which varying concentrations of the seawater mineral extract (0.1% to 1.5%) were added with measurements being taken over a period of 2-15 hours.

Figure 5:
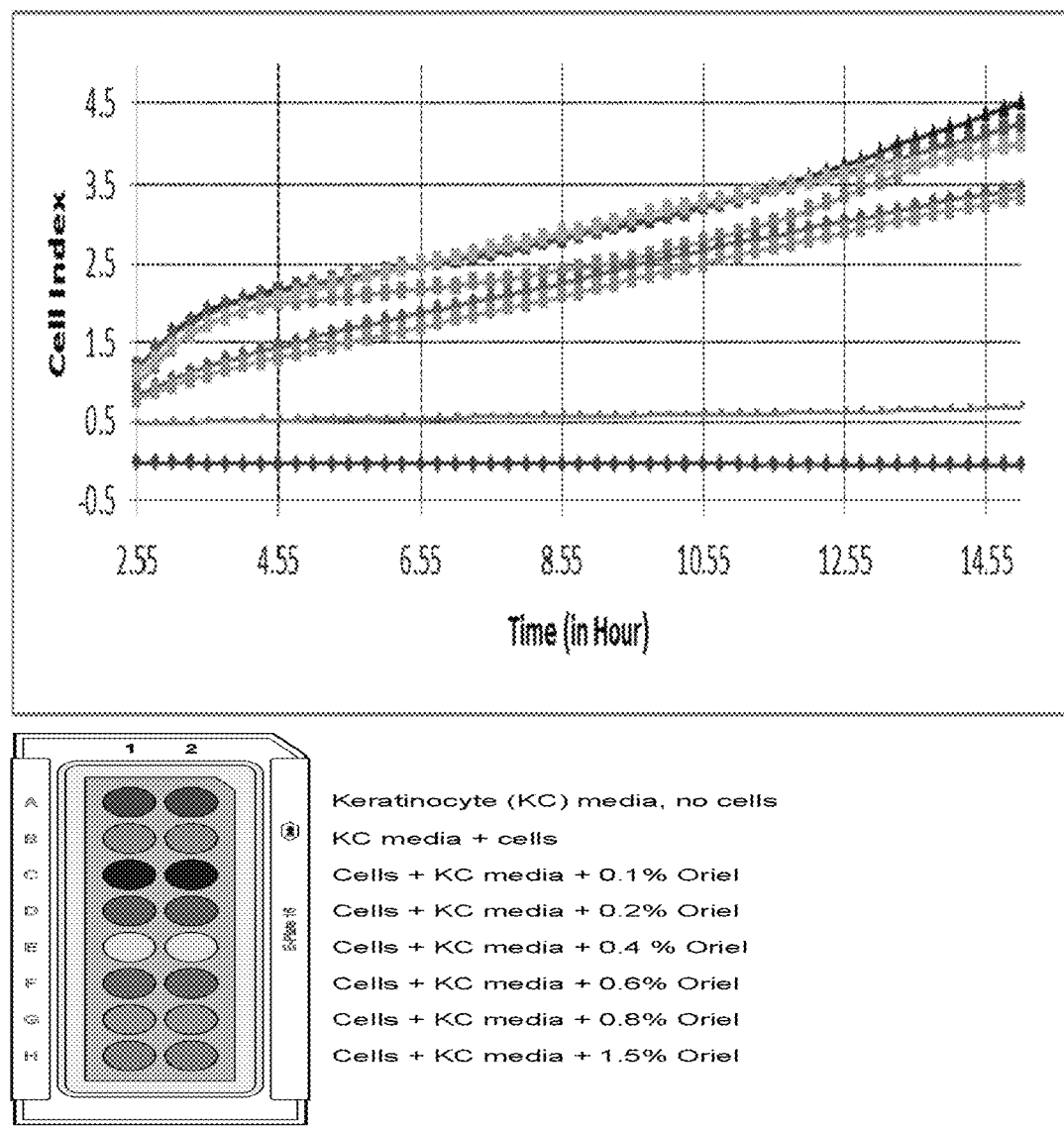
FIG. 5 shows Real-Time Cellular Adhesion Dynamics and Turnover of Primary Human Dermal Keratinocytes in response to the seawater mineral extract of the present invention.

Graphical representation of cell adhesion dynamics is outlined in FIG. 5, which represents the Keratinocyte cell-ECM adhesion turnover (making and breaking of cell interactions). It can be seen that the seawater mineral extract promotes cell adhesion formation above and beyond that of Control, between 4.5 hours and 15 hours—at three concentrations—0.1%, 0.2% and 0.4%. The seawater mineral extract at concentrations of 0.6% and 0.8% slightly reduces the rate of adhesion formation, but only modestly when compared to control cells. The response observed for the seawater mineral extract at 0.1%, 0.2% and 0.4%, is indicative of increased cell spreading (activation of the GTPase—RAC1) and this increase in Focal Contact, Focal Complex and Focal Adhesion formation is a highly dynamic process, highlighting the bioactive capacity of the "seawater" extract. It can be observed that control Keratinocytes loose traction within the ECM complex between 4.5 hours and 12.5 hours (reduction in Cell Index), while it is maintained at 0.1%, 0.2% and 0.4% of the "seawater" extract.

All concentrations of the seawater mineral extract displayed an increase in cell adhesion kinetics and dynamics. The findings elucidated in highlight the potential of the seawater mineral extract in regenerative and healing processes in the skin.

Example 14

Real Time Adhesion and Adhesion Dynamics of Primary Human Dermal Fibroblasts

Real-Time Cellular analysis was carried out on Primary Human Dermal Fibroblasts. Cell were grown on a 2.5-

Dimensional Extra Cellular Matrix environment as a model of skin tissue, to which varying concentrations of the seawater mineral extract (0.1% to 1.5%) were added with measurements being taken over a period of 2-3 hours.

Figure 6:
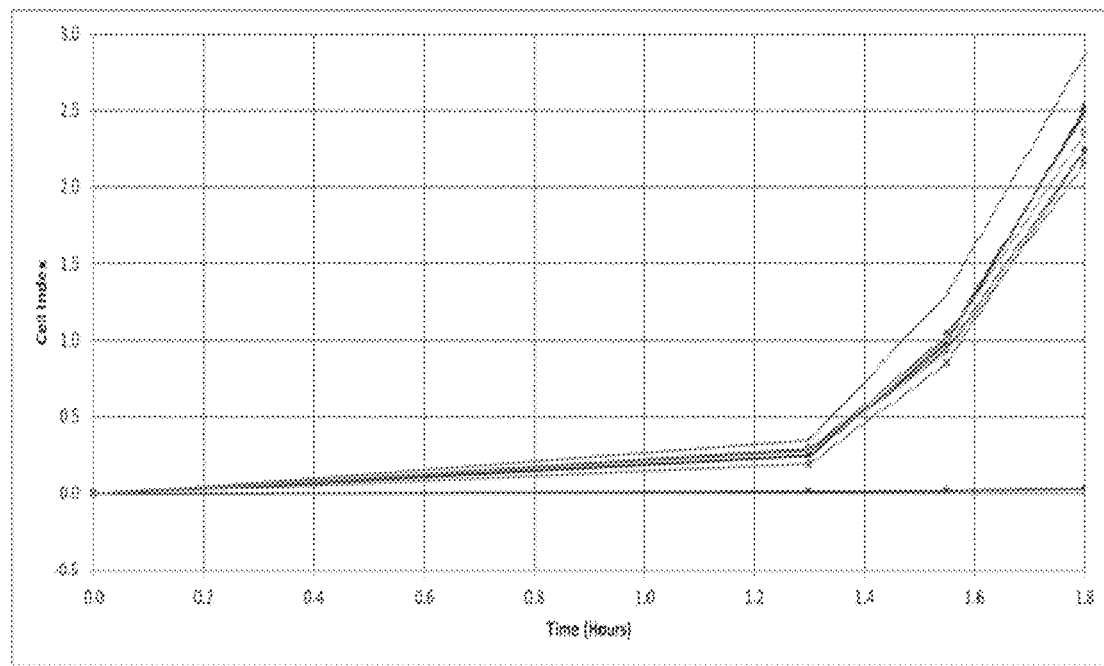
FIG. 6 shows Real-Time Cellular Adhesion Dynamics and Turnover of Primary Human Dermal Fibroblast, in response to the seawater mineral extract of the present invention.
Figure 6:
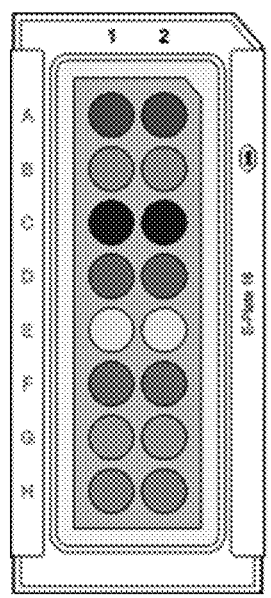

Cell adhesion kinetics displayed a biphasic effect with Dermal Fibroblasts, but at all concentration (0.1% to 1.5%) cell adhesion dynamics (kinetics/rate and extent) was greater than control fibroblasts (FIG. 6). Initial adhesion was slow (0-1.3 hours), but increased exponentially from 1.3 hours to 1.6 hours, with all concentrations of the seawater mineral extract having a potentiating effect, indicating a potential beneficial effect of wound healing and skin regeneration.

Figure 7:
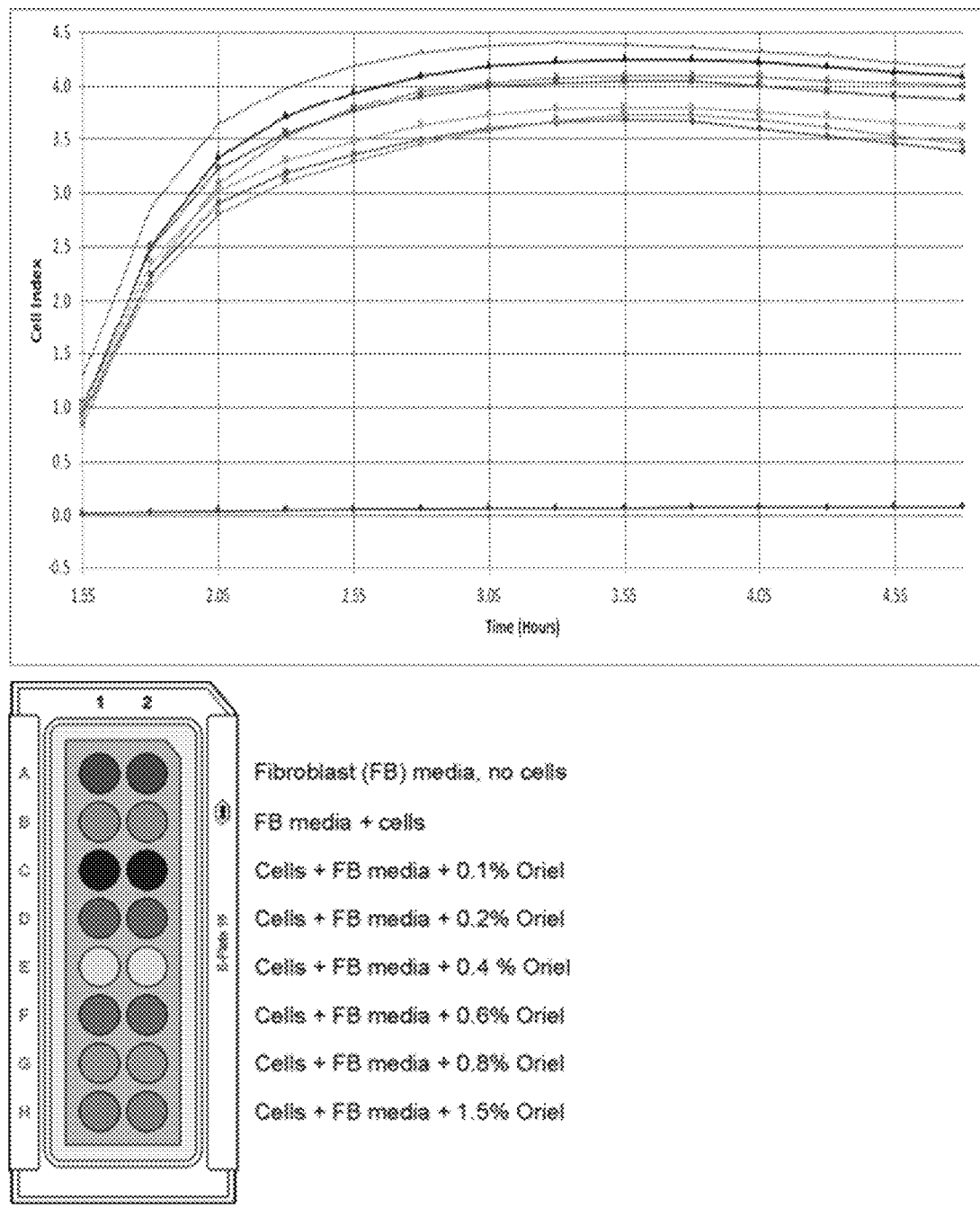
FIG. 7 shows Real-Time Cellular Spreading Dynamics and Turnover of active Primary Human Dermal Fibroblast Cell in response to the seawater mineral extract of the present invention.

Cell spreading dynamics (1.6 hours to 3 hours) again displayed a potentiating effect of the seawater mineral extract on active cell spreading (FIG. 7). Similar to the keratinocyte studies, this has implications for cellular architecture and rigidity (i.e. Tensegrity, form and function of cytoskeletal architecture etc.), and thus biomechanical properties of skin (elasticity, tone, firmness). Interestingly, the highest concentration of the seawater mineral extract demonstrated the most profound beneficial effect in this regard, followed by the two lowest concentrations (0.1% and 0.2%). 0.4% to 0.8% concentrations displayed a slightly reduced cell spreading.

The lowest and highest concentration of OMMC elicited the greatest level of cell spreading at the 3 hour time point. These differences where abrogated at later time points when all concentrations of OMMC resulted in rates and levels of cell proliferation and spreading greater to or equal to control fibroblast culture.

Figure 8:
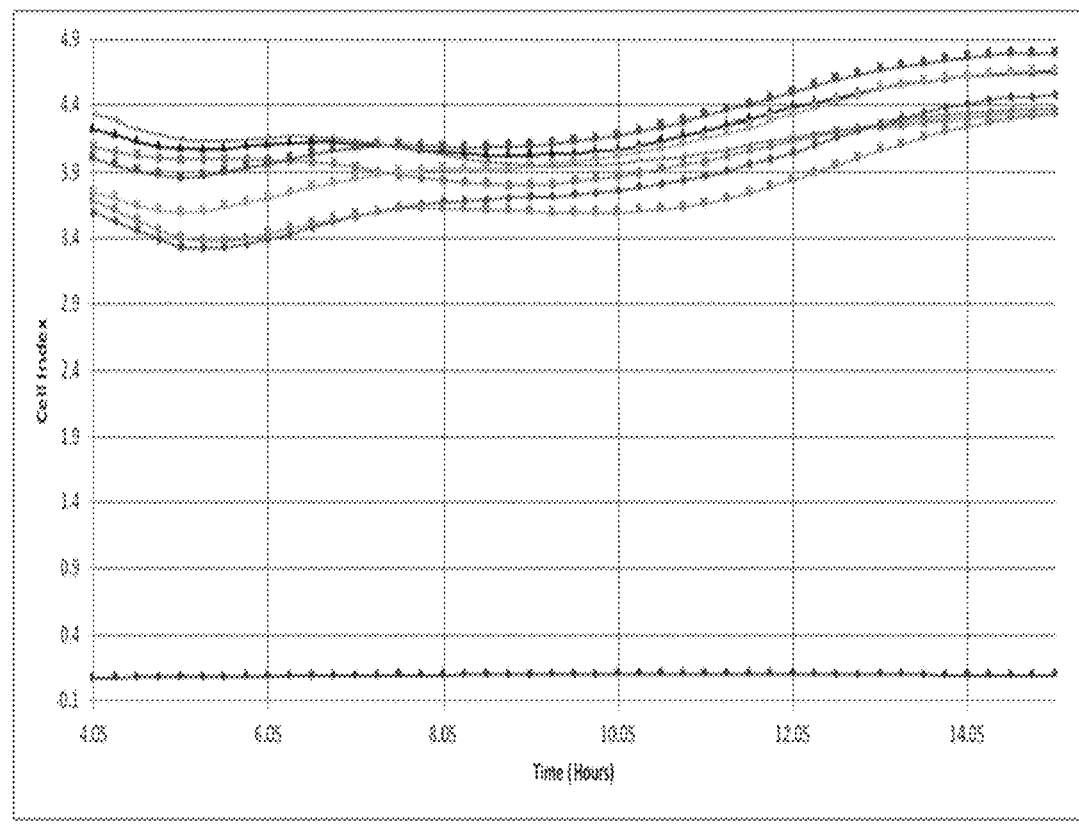
FIG. 8 shows Real-Time Cellular Proliferation and Integration of active Primary Human Dermal Fibroblast Cell in response to the seawater mineral extract of the present invention.
Figure 8:
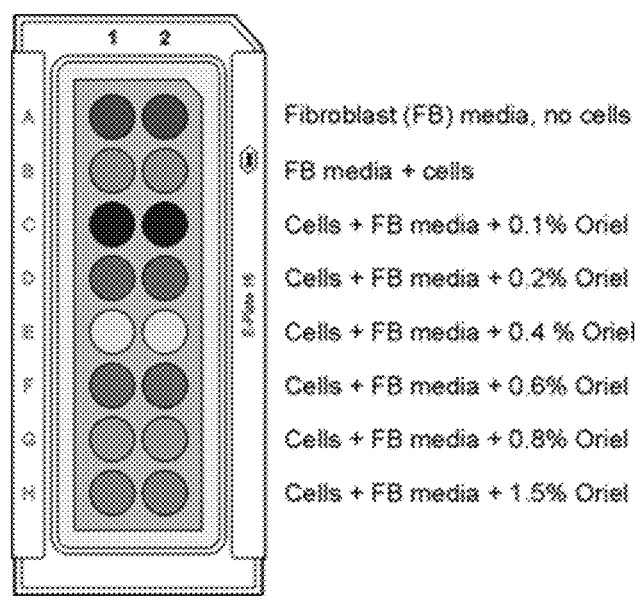

This reduction was overcome after the 3 hour time point, when all concentrations (bar the 0.6% and 0.8%) displayed an increased cellular integrity within the ECM, and an improved cell proliferation profile (FIG. 8). The 0.6% and 0.8% concentrations gave the same cell index as the control Dermal Fibroblasts.

All concentrations of OMMC, bar the two highest (0.8 and 1.5%) exhibited a greater integration, cell growth and surface coverage when compared to control fibroblast culture.

Overall, these experiments demonstrate that the seawater mineral extract has the potential to improve fibroblast cell health and dynamics, improve wound healing and regenerative capacity, and improve the biomechanical properties of the skin.

Example 15

Synergy Study

In a synergy study in vivo platelet analysis (aggregation and adhesion studies using the IMPACT-R cone and platelet analyser) along with PMP analysis using flow cytometry and CD62-P staining (P-Selectin+PMPs) is carried out with the ionised seawater mineral extract and non-ionised, but otherwise comparable, mineral compositions.

Initial indications suggest that the combination of the ionised seawater mineral extract has higher potency and superior and improved bio-availability over other commercially available non-ionised mineral compositions.

Example 16

Comparative Study

In a comparative study in vivo platelet analysis (aggregation and adhesion studies using the IMPACT-R cone and platelet analyser) along with PMP analysis using flow cytometry and CD62-P staining (P-Selectin+PMPs) is carried out with the seawater mineral extract and a number of other commercially available and premium magnesium products.

Initial indications suggest that the combination of the seawater mineral extract has higher potency and superior and improved bio-availability over other commercially available mineral compositions.

Example 17

Flow Mediated Dilation

The seawater mineral extract was tested in a standard Fibromuscular dysplasia (FMD) test model. A baseline reading was taken with a resting diameter of 4.5 mm. A pressure cuff was then applied and 45-60 seconds after release a blood vessel diameter of 5.0 mm and a reading of 11% FMD. Nitroglycerin was used as a positive control, 4 minutes after administration in blood vessel diameter of 5.3 mm and a reading of 10% FMD was achieved. The seawater mineral extract was then applied at 6 hour intervals of 0.5 ml of mineral extract left for the same length of time as the positive control.

The seawater mineral extract was found to increase FMD by 3.8% and demonstrated a 24% overall improvement in vascular function (data not shown).

Example 18

Sheer Stress and Vascular Oxidative Stress

The effects of the seawater mineral extract on sheer stress and vascular oxidative stress were tested using a standard perfusion pump coupled with a fluidic unit (Ibidi®) capable of simulating laminar and oscillatory flow.

Following flow exposure, the Bovine Aortic Endothelial Cells (BAECs) were incubated with Dihydroethidium Bromide (DHE.A). The cells were then collected, washed and fixed in 2% paraformaldehyde for 10 min and re-suspended in 0.5 ml of PBS with 2% FBS and analysed by fluorescent microscopy.

Figure 9:
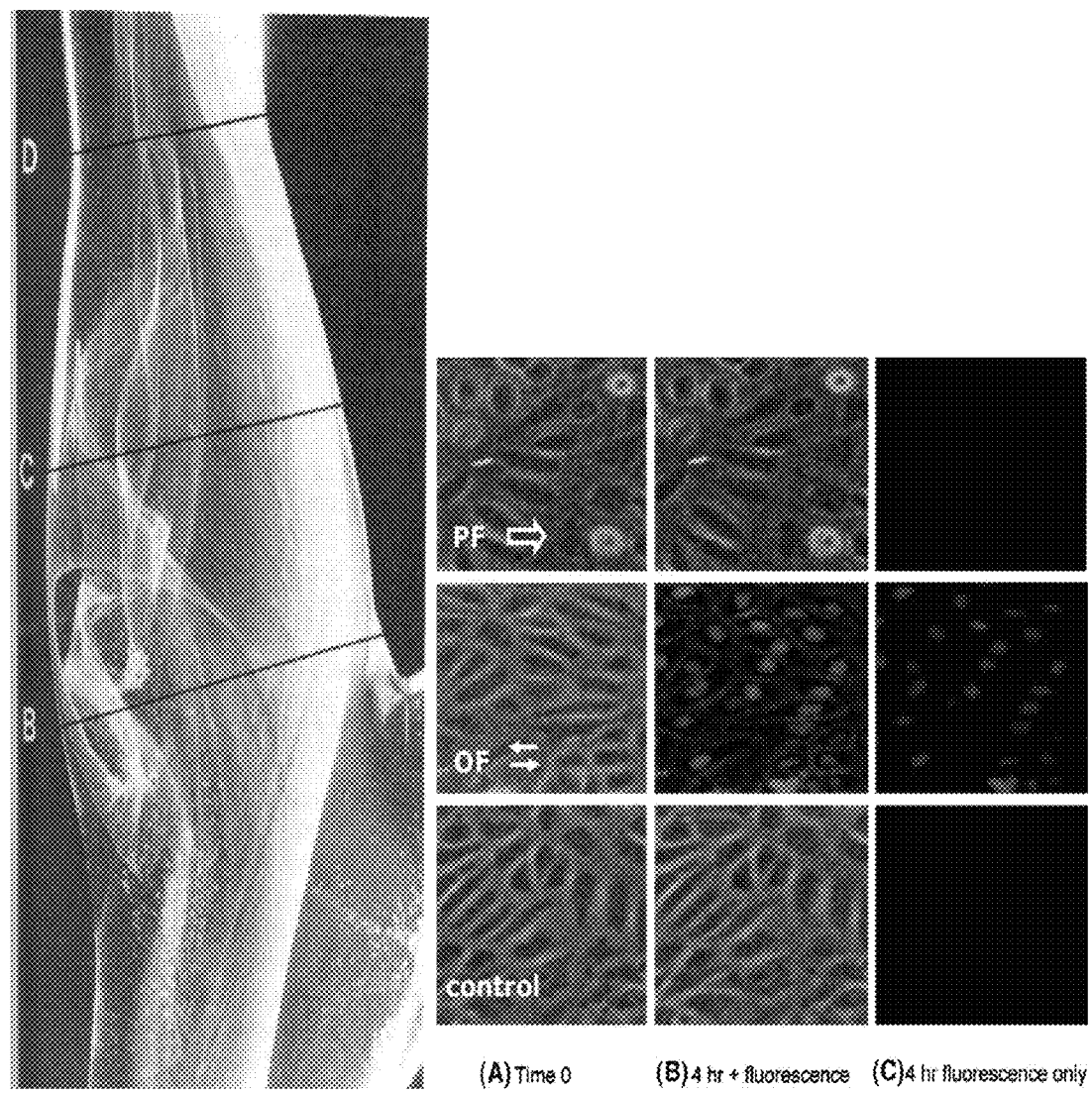
FIG. 9 shows real-time intracellular superoxide production in response to flow measured by DHE. A.

Using a flow cytometer, DHE.A was excited and fluorescence emission was measured. Relative fluorescence intensity was used as measurement of superoxide production. As shown in FIG. 9 at time zero, column A illustrates BAECs under 3 conditions: pulsatile flow (PF), oscillatory flow (OF), and static state (control).

The seawater mineral extract was applied at a concentration of between 0.1-0.5% and incubated for 4 hours.

The seawater mineral extract has been shown (FIG. 9) to reduce superoxide release and subsequently has the potential to improve vascular oxidative stress.

Example 19

Vascular Inflammation

Vascular endothelial cell inflammation was induced, driving over expression of TRPM7 as assessed by qRT-PCR.

No increase of TRPM7 & was observed in seawater mineral extract treated ECs as assessed by qRT-PCR.

Example 20

Stem Cell

Clinical studies were conducted in which patients were administered the seawater mineral extract 0.5 ml thrice daily, for 4 weeks. Analysis was undertaken using proprietary quantitative and qualitative flow cytometric analysis on a FC500 cytometer (Beckman-Coulter). Levels of Progenitor cells (Cd34+CD45dim) and Endothelial progenitors (EPC) were measured as a % of CD45+ events and also as cells/mL. Levels of and Angiogenic lymphocytes were measured by % of CD3+ events that are positive for CD31.

An increase in circulating stem cell levels and circulating progenitor cell levels in humans was observed.

Total progenitor cells were increased from a pre-sample of 0.037% (2172 cells/mL) to a Post-intervention sample of 0.062% (4094 cells/mL). Circulating levels of Endothelial progenitors were increased from a pre-sample of none to a Post-intervention sample of 0.008%, (528 cells/mL). Supplementation with the seawater mineral extract led to a 9% increase in circulating Angiogenic lymphocytes from a pre-sample of 35% to a Post-intervention of 44% (no data shown).

Example 21

Patient Case Study of the Effect of the Super-Concentrated Seawater Mineral Extract According to Example 3 on Arthritis This study was carried out on two patients:

Patient 1: Male, age 61, suffering from diagnosed Chronic Arthritis with severely reduced mobility and movement in hands, knees and other joints.

Injections of the super-concentrated seawater mineral extract according to example 3 were administered to the patient every two weeks.

Patient 2: Male, age 41, suffering from mild Arthritis in the right hand knee. Patient plays football and feels the need for prolonged warm-ups and cool downs to relief stiffness and pain associated with the mild Arthritis. Post-match patient often notices that his knee locks with relief achieved only through hot baths and deep heat. A gel comprising the super-concentrated seawater mineral extract according to Example 3 at a concentration of 0.33% was directly applied to the skin surface around the knee joint 30 minutes prior to a football match.

Results:

Patient 1:

Week 1: Noticeable improvement in ease of joint movement

Week 2: Significant improvement in mobility. No more clicking of bones in knee when standing up. Reduction in pain.

Week 3: Experiencing muscle growth where he has had muscle wastage

Week 4: Increase in muscle around knee which gives support to knee and has led to significant reduction in pain in knee Week 5: Patient can now put pressure on his knee.

Patient 2: Observed that only normal warm-up were needed and knee did not lock-up after the match such that further hot bathes and deep heat treatment were not required.

In conclusion the super-concentrated seawater mineral extract according to Example 3 appears to have a significant effect on Arthritis.

Example 22

Patient Case Study of the Effect of the Super-Concentrated Seawater Mineral Extract According to Example 3 on Psoriasis, Eczema, Acne and Cradle Cap This study was carried out on five patients:

Patient 1: Female, age 50, suffering from diagnosed Psoriasis all over body since childhood. A gel comprising the super-concentrated seawater mineral extract according to Example 3 at a concentration of 0.33% was directly applied to the skin surface affected by the skin disorder twice daily over a 4 week period.

Patient 2: Female, age 18, affected by Eczema on both arms for 12 years. A gel comprising the super-concentrated seawater mineral extract according to Example 3 at a concentration of 0.33% was directly applied to the skin surface affected by the skin disorder twice daily over 4 days.

Patient 3: Female, age 46, suffering from psoriasis in multiple sites for many years. A gel comprising the super-concentrated seawater mineral extract according to Example 3 at a concentration of 0.33% was directly applied to the skin surface affected by the skin disorder twice daily over a 2 week period.

Patient 4: Female, age 16, suffering from mild to medium back acne. A gel comprising the super-concentrated seawater mineral extract according to Example 3 at a concentration of 0.33% was directly applied to the skin surface affected by the skin disorder twice daily over a 1 week period.

Patient 5: Female, age 6 months, suffering from Cradle Cap. Dry scalp combed away and a gel comprising the super-concentrated seawater mineral extract according to Example 3 at a concentration of 0.33% was directly applied to the skin surface affected by the skin disorder twice daily for 2 days.

Results:

Patient 1: The first patient noticed a significant improvement including new healthy skin growth in areas where Psoriasis was active by week 4.

Patient 2: The second patient's skin was cleared of eczema in 4 days. Additionally eczema did not affect the patient's skin during a period of 8 weeks subsequent to the treatment.

Patient 3: The third patient noticed a reduction in size of the affected areas within 2 weeks.

Patient 4: The fourth patient noticed that acne had cleared in four days. No reoccurrence has been observed during a period of 6 weeks subsequent to treatment.

Patient 5: Cradle Cap was observed to have cleared.

In conclusion the super-concentrated seawater mineral extract according to Example 3 appears to have a significant effect on Psoriasis, Eczema, Acne and Cradle Cap.

Example 23

Figure 10A:
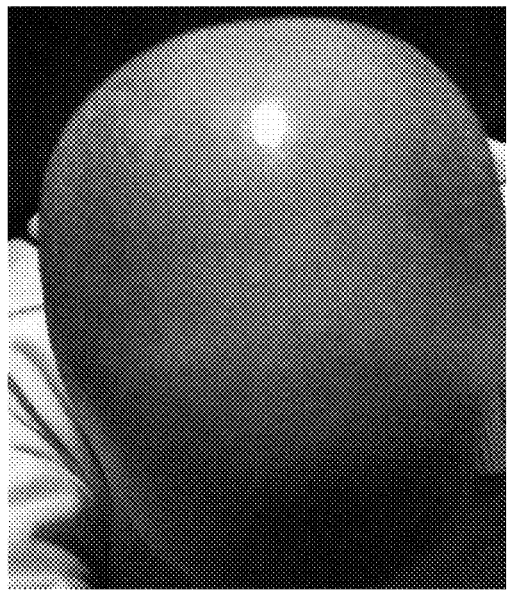
FIG. 10a is a photograph of the head of a patient suffering from hair loss before treatment with a gel comprising a super-concentrated seawater mineral extract according to the invention.

Patient Case Study of the Effect of the Super-Concentrated Seawater Mineral Extract According to Example 3 on Stimulating Hair Growth and Hair Regeneration This study was carried out on two patients:

Patient 1: Male (Age 50) suffering from hair loss (as shown in FIG. 10a), more particularly bald on front side temples for 20 years and bald on crown for 15 years. The patient shaves his head regularly. A Gel comprising the super-concentrated seawater mineral extract according to Example 3 at a concentration of 0.33% was directly applied twice daily for 8 weeks to the skin surface affected by the hair loss.

Patient 2: Female (Age 66) who suffers from thinning and wispy hair. A Gel comprising the super-concentrated seawater mineral extract according to Example 3 at a concentration of 0.33% was directly applied twice daily for 5 weeks to the skin surface affected by the hair loss.

Figure 10B:
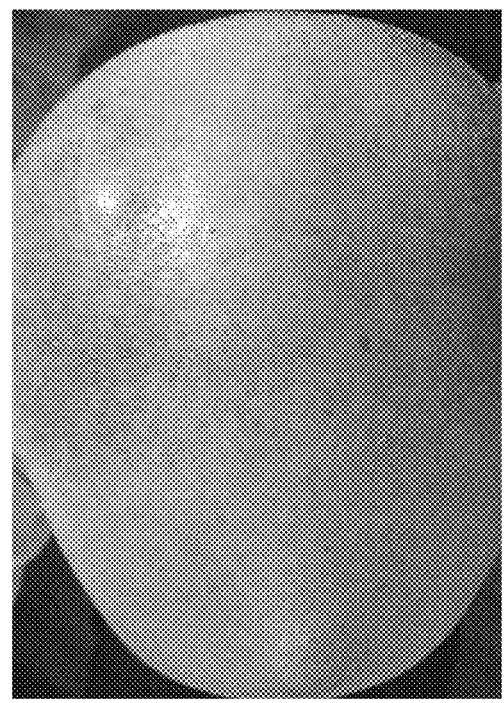
FIG. 10b is a photograph of the head of the patient suffering from hair loss after treatment with a gel comprising a super-concentrated seawater mineral extract according to the invention.

Results:

Patient 1: After 4 weeks hair growth on crown is noticeable and firm and hair growth on front temples is fine and very early stage (as shown in FIG. 10b).

Patient 2: After 5 weeks hair growth and condition is noticeable and is fuller and thicker. Patient's hairdresser commented that it was in the best condition she had ever seen it.

In conclusion the super-concentrated seawater mineral extract according to example 2 appears to have a significant effect on hair growth and hair regeneration.

Example 24

Patient Case Study of the Effect of the Super-Concentrated Seawater Extract According to Example 3 on Muscle Repair and Recovery This study was carried out on three patients, Male Personal Training Coaches Aged 30 to 34. The patients were suffering from heavy muscle burn after workouts. Electrolyte loss after participation in athletic events.

A Gel comprising the super-concentrated seawater mineral extract according to Example 3 at a concentration of 0.33% was directly applied to the skin surface affected by the muscle pain and disorder over a four week period.

Results:

Significantly reduced muscle pain due to muscle burn, faster recovery post workout. Significant Electrolyte replacement.

In conclusion the super-concentrated seawater mineral extract according to Example 3 appears to have a significant effect on muscle repair and recovery after intense efforts.

Example 25

Patient Case Study of the Effect of the Super-Concentrated Seawater Mineral Extract According to Example 3 on Nerve Damage This study was carried out on two patients:

Patient 1: Female, age 54, experiencing sharp constant pain in shoulder and neck. The patient was on Difene® painkillers.

Patient 2: Female, age 18, with an injured shoulder from about 4 years ago. X-rays show no damage but the patient had a constant dull pain in shoulder.

Both patients directly applied a gel comprising the super-concentrated seawater mineral extract according to Example 3 at a concentration of 0.33% twice daily for 2 weeks to the skin surface of the shoulder and/or neck.

Results:

Patient 1: The first patient noticed a significant reduction in pain by about 50% was observed by the end of week one and by week 2 does not feel any sharp pain and the pain killer treatment could be stopped.

Patient 2: The second patient's pain is completely gone by week 2 of treatment.

Both patients continue to use the gel once daily.

In conclusion the super-concentrated seawater mineral extract according to Example 3 appears to have a significant effect on decreasing pain resulting from nerve damage or injury.

Example 26

Clinical Study of the Effect of the Super-Concentrated Seawater Mineral Extract According to Example 2 on Recovery on Skin Damage Following Cancer Radiotherapy This study was carried out on one patient female, age 48 that had to undergo chemotherapy and radiation treatment for breast cancer. The patient experienced red itchy skin, blisters and skin burning sensation. Particular sore areas were the scar tissue, nipple area and underarm.

A Gel comprising the super-concentrated seawater mineral extract according to Example 3 at a concentration of 0.33% was directly applied three times daily for 4 weeks to the sore areas and the areas surrounding the sore areas.

Results:

The gel had an immediate soothing effect. The patient felt significant reduction of the burning sensation and itchiness. After three weeks of treatment the burning sensation ceased and the redness decreased significantly. Furthermore the scar tissue is moist and the skin healed and renewed around the scars.

Patient continues to use the gel and now uses oral drops comprising the extract of the present invention.

In conclusion the super-concentrated seawater mineral extract according to Example 3 appears to have a significant effect on decreasing pain and skin disorders resulting from cancer treatment.

Example 27

Patient Case Study of the Effect of the Super-Concentrated Seawater Mineral Extract According to Example 2 on Ulcerative Colitis and Digestion This study was carried out on two patients:

Patient 1: Female, age 34 suffering from digestive upset and severe ulcerative Colitis affecting overall body performance, skin condition, and hair condition, and recovery time from illness. Ten drops of an oral composition of the extract, taken twice daily under tongue over a 4 week period.

Patient 2: Male, age 43. No particular complaints but wanted to try the extract. Ten drops of an oral composition of the extract, taken twice daily under tongue over a 2 week period.

Results:

Patient 1: Noticeable improvement in digestive ability with food tasting better by week 2. Improved overall health with stronger, fuller hair and improved skin condition observed. Patient noticed an improvement of 50% on recovery from illness.

Patient 2: After 2 weeks noticed an improvement in overall health and digestive ability, with food tasting better. Generally felt better, more energetic and thinking clearer.

Example 28

Patient Case Study of the Effect of the Super-Concentrated Seawater Mineral Extract According to Example 2 on Rosea This study was carried out on two patients:

Patient 1: Female, age 49, suffering from severe Rosea coupled with a lot of broken veins on both cheeks. A gel comprising the super-concentrated seawater mineral extract according to Example 3 at a concentration of 0.33% was applied twice daily for 3 weeks to the affected areas.

Patient 2: Female, age 48, suffering from Rosea A gel comprising the super-concentrated seawater mineral extract according to Example 3 at a concentration of 0.33% was applied daily.

Results:

Patient 1: By week 3, patient noticed that Rosea was noticeably reduced after 15 mins after application and remained reduced until the following day.

Patient 2: Patient noted excellent results.

Example 29

Patient Case Study of the Effect of the Super-Concentrated Seawater Mineral Extract According to Example 2 on Migraine This study was carried out on one patient (Male, age 48) with a family history of Migraines, Strokes and Bleeds on the brain, suffering from a persistent mild throbbing headache present 80% of the time. Migraine becomes severe and in need of pain relief about a couples per week. Ten drops of an oral composition of the extract, taken twice daily under tongue over a 4 week period.

Results:

By week 2, patient observed that the persistent throbbing had ceased and at week 4 was still free from headaches.

Example 30

Patient Case Study of the Effect of the Super-Concentrated Seawater Mineral Extract According to Example 2 as Aftersun This study was carried out on one patient (Male, age 38), suffering from a burning sensation after exposure to the sun on his head. Patient is bald. Patient applied a gel comprising the super-concentrated seawater mineral extract according to Example 3 at a concentration of 0.33% twice, once immediately after exposure, and once a few hours later.

Results:

Patient noted immediate relief and suffered no sunburn the next day.

Example 31

Patient Case Study of the Effect of the Super-Concentrated Seawater Mineral Extract According to Example 2 on Insomnia This study was carried out on one patient. A gel comprising the super-concentrated seawater mineral extract according to Example 3 at a concentration of 0.33% was applied on the inside of elbows and behind the ears.

Results:

The gel was noted to act as an excellent sleeping aid.

Example 32

Patient Case Study of the Effect of the Super-Concentrated Seawater Mineral Extract According to Example 2 on Rapid Cycling Bi-Polar Disorder The study was carried out on a 40 yr old female patient with a 13 year history of bi-polar disorder. The patient suffered from extreme anxiety and insomnia due to the condition and medical treatments which had led to hospitalisation. The patient took the mineral as a supplement in water and experienced a noticeable and significant improvement in her condition after just five days.

The patient continues to improve and continues to take the mineral extract.

In this specification the terms "include" and "comprise" and any grammatical variations thereof are used interchangeably and should be accorded the widest possible interpretation.

The invention is not limited to the embodiments described above but may be varied in both construction and detail within the scope of the appended claims.

The invention claimed is:

1. Method of making a seawater mineral extract derived from naturally sourced seawater having a salinity of from 3.4% Brix to 3.6% Brix, wherein the seawater mineral extract comprises a mineral salt content of from 25% to 55% of the overall seawater mineral extract by weight, wherein the seawater mineral extract is an inorganic concentrated liquid ionized composition having a free ion state magnesium concentration of at least 40 g/L wherein, the method comprises the following steps:
   (a) harvesting and processing seawater to form a super-concentrated sea water, by
      i collecting sea water from a sea or ocean source;
      ii filtering the sea water of step (a)i to remove algae, plankton and other plant materials microorganisms and impurities;
      iii passing the filtered water of step (a)ii through a high-pressure reverse osmosis membrane to separate the sea water into desalinated sea water and concentrated sea water;
      iv delivering the concentrated sea water of step (a)iii into an evaporator, heating the concentrated sea water under vacuum to produce a slurry formed of calcium sulphate, sea salt and a super concentrated sea water;
      v delivering the slurry of calcium sulphate, sea salt and a super concentrated sea water of step (a)iv into a centrifuge for separating the slurry into the individual separate components of calcium sulphate, sea salt and a super concentrated sea water; and,
   (b) further processing the super concentrated sea water of step (a) as follows:
      i removing from 40% to 75% of the total sodium content contained in the super concentrated seawater of step (a)v to produce a super concentrated sea mineral liquor;
      ii adding the super concentrated sea mineral liquor of step (b)i to a suitable carrier, vehicle or solvent; and,
      iii adding a chelating agent to the super concentrated sea mineral liquor of step (b)ii;
      such that, the resulting seawater mineral extract comprises the super concentrated sea mineral liquor in ionic liquid form whereby ions are held in their free ion state, resulting in the seawater mineral extract having an oily and lubricating texture, the suitable carrier, vehicle or solvent, and the chelating agent.

2. The method of making the seawater mineral extract as claimed in claim 1 wherein, the super concentrated sea mineral liquor is added to the carrier, vehicle or solvent at a concentration from 0.01% to 5% by volume.

3. A method of making the seawater mineral extract as claimed in claim 1, wherein the sea or ocean source is a sublittoral portion of a neritic province of a euphotic zone.

4. The method of making the seawater mineral extract as claimed in claim 1, wherein magnesium and sodium are present in the seawater mineral extract at a ratio of at least 2:1.

5. The method of making the seawater mineral extract as claimed in claim 1, wherein the mineral salt content comprises:
free ion state magnesium at a concentration of from 62 g/L to 95 g/L;
free ion state sodium at a concentration of from 22 g/L to 28 g/L;
free ion state potassium at a concentration of from 21 g/L to 26 g/L;
free ion state boron at a concentration of at from 0.20 g/L to 0.23 g/L; and,
free ion state calcium at a concentration of from 0.070 g/L to 0.087 g/L.

6. The method of making the seawater mineral extract as claimed in claim 1, wherein the mineral salt content comprises one or more of nickel, copper, strontium, molybdenum, iron, zinc, aluminum, manganese, barium, vanadium, chromium, arsenic, antimony, beryllium, cobalt, selenium, cadmium, tin, mercury, thallium and lead.

7. The method of making the seawater mineral extract as claimed in claim 1, wherein said seawater mineral extract comprises free ion state magnesium at a concentration of between 62 g/L and 95 g/L.

8. The method of making the seawater mineral extract as claimed in claim 1, wherein said seawater mineral extract comprises free ion state sodium at a concentration of between 15 g/L and 28 g/L.

9. The method of making the seawater mineral extract as claimed in claim 1, wherein said seawater mineral extract comprises free ion state potassium at a concentration of between 18 g/L and 26 g/L.

10. The method of making the seawater mineral extract as claimed in claim 1, wherein said seawater mineral extract comprises free ion state boron at a concentration of between 0.18 g/L and 0.26 g/L.

11. The method of making the seawater mineral extract as claimed in claim 1, wherein said seawater mineral extract comprises free ion state calcium at a concentration of between 0.075 g/L and 0.09 g/L.

* * * * *